United States Patent [19]

Barnes

[11] Patent Number: 5,436,149
[45] Date of Patent: Jul. 25, 1995

[54] THERMOSTABLE DNA POLYMERASE WITH ENHANCED THERMOSTABILITY AND ENHANCED LENGTH AND EFFICIENCY OF PRIMER EXTENSION

[76] Inventor: Wayne M. Barnes, 223 Renaldo Dr., Chesterfield, Mo. 63017

[21] Appl. No.: 21,623

[22] Filed: Feb. 19, 1993

[51] Int. Cl.⁶ .................. C12N 9/12; C12N 15/54; C12P 19/34; C12P 19/30
[52] U.S. Cl. .................. 435/194; 435/91.2; 435/91.5; 935/17
[58] Field of Search ............ 435/91, 194, 172..3, 435/252.1, 91.1, 91.2, 91.4, 91.5, 193; 935/16

[56] References Cited

U.S. PATENT DOCUMENTS

| | | | |
|---|---|---|---|
| 4,683,202 | 7/1987 | Mullis | 435/91.2 |
| 4,795,699 | 1/1989 | Tabor et al. | 435/5 |
| 4,921,794 | 5/1990 | Tabor et al. | 435/91.2 |
| 5,001,050 | 5/1991 | Blanco et al. | 435/5 |
| 5,075,216 | 12/1991 | Innis et al. | 435/6 |
| 5,079,352 | 1/1992 | Gelfand et al. | 536/23.2 |

FOREIGN PATENT DOCUMENTS

WO/06200 4/1992 WIPO.

OTHER PUBLICATIONS

Mattila, P. et al. *Nucl. Acids Res.* 19(18):4967–4973. (1991).
Lundberg, K. S. *Gene* 108:1–6 (1991).
Cheng, S. et al. *PNAS* 91:5695–5699 (1994).
Barnes, W. M. *PNAS* 91:2216–2220 (1994).
Barnes "The fidelity of Taq polymerase catalyzing PCR is improved by and N-terminal deletion", Gene, 112(1992) 29–35.

*Primary Examiner*—Robert A. Wax
*Assistant Examiner*—Dian C. Jacobson
*Attorney, Agent, or Firm*—Senniger, Powers, Leavitt and Roedel

[57] ABSTRACT

A DNA polymerase having an amino acid sequence comprising substantially the same amino acid sequence as that of *Thermus aquaticus* or *Thermus flavus* DNA polymerase, excluding the N-terminal 280 amino acid residues of *Thermus aquaticus* DNA polymerase or the N-terminal 279 amino acid residues of *Thermus flavus* DNA polymerase, recombinant DNA sequences encoding said DNA polymerases, vectors comprising said DNA sequences, and host cells containing such vectors. A formulation of thermostable DNA polymerases comprising a majority component comprised of at least one thermostable DNA polymerase of the type described above, wherein the DNA polymerase lacks 3'-exonuclease activity, and a minority component comprised of at least one thermostable DNA polymerase exhibiting 3'-exonuclease activity, and an improved method for amplifying nucleic acid sequences by polymerase chain reaction wherein the above formulation is mixed and used to catalyze primer extension, are also provided.

16 Claims, 10 Drawing Sheets

Figure 1A

```
         NcoI         10        20        30              KT1 36MER (SEQ
                                                                  ID NO: 1)
GAGCCATGGGGCCTCCTCCACGAGTTCGGCCTTCTGG
   ***  ||||||||||||||||||||||||||||||||||   <-- upper case are
   m  g  L  L  H  E  F  G  L  L  E ...       <-- codon numbering for
WT aa
     278 280 282 284 286 288
WT aa
AGTTTGGCAGCCTCCTCCACGAGTTCGGCCTTCTGG ...       (SEQ ID NO: 14)
         959 969 979                          TaqPol.seq GenBank
entry
Accession No. J04639 (numbering includes 5' non-translated
region)
```

Figure 1B

```
--other strand-- KLENTAQ32 35mer  (SEQ ID NO: 3)
                          HindIII
                 26   16 ****** 6
GGACTGGCTCTCCGCCAAGGAGTAGTAAGCTTCGC
||||||||||||||||||||||||||||  ||
   D  W  L  S  A  K  E  *
  826 828 830 832
GGACTGGCTCTCCGCCAAGGAGTGATACCACC         (SEQ ID NO: 15)
2604 2614 2624
TaqPol.seq
```

Figure 2

```
         10        20        30
GAGCCATGGGCCTCCTCCTCCACGAGTTCGGCCTTCTGG    KT1 36MER (SEQ ID NO: 1)
    ***  ||||||||||||||||||||||||||| |||        <-- upper case are
       m g L L H E F G L L E ...                <-- codon numbering for
WT aa   278 280 282 284 286 288
WT aa
AGTTTGGAAGCCTCCTCCTCCACGAGTTCGGCCTTCCTGG   Tfl.seq (SEQ ID NO: 16)
GenBank 1387      1397      1407            entry Accession number
X66105                                      (numbering includes 5' non-translated
                                            region)

26        16         6
GGACTGGCTCTCCGCCAAGGAGTAGTAAGCTTCGC         --other strand--
|||||||||||||||||||||||||||||||| |             KLENTAQ32 35mer
  D W L S A K E *
  826 828 830
GGACTGGCTCTCCGCCAAGGAGTAGGGGGGTCCTG         Tfl.seq (SEQ ID NO: 17)
 3032      3042      3052
```

FIG. 3
2 min. at indicated 99°, 98° or 97°, 10 min. 65° per cycle, 20 cycles.
99°    AmpliTaq    KlenTaq1
      .8   .4   .2    1/4   1/8   1/16    <-- ul per 100 ul reaction.
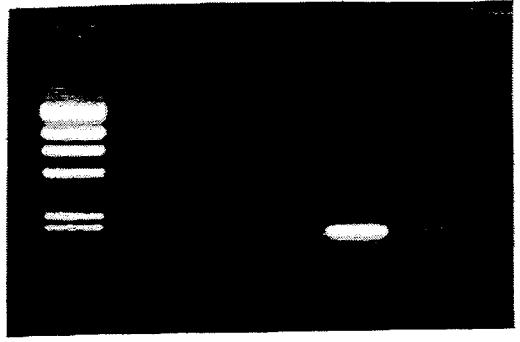
<-- 2 KB product size
98°    AmpliTaq    KlenTaq1
      .8   .4   .2    1/4   1/8   1/16    <-- ul per 100 ul reaction.
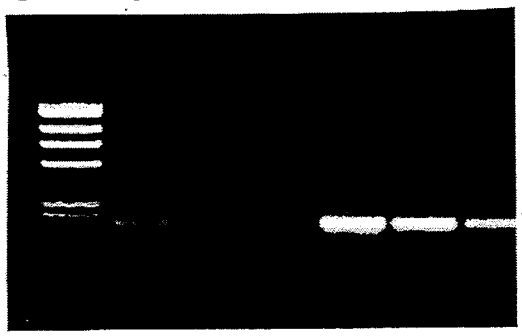
<-- 2 KB product size
97°    AmpliTaq    KlenTaq1
      .8   .4   .2    1/4   1/8   1/16    <-- ul per 100 ul reaction.
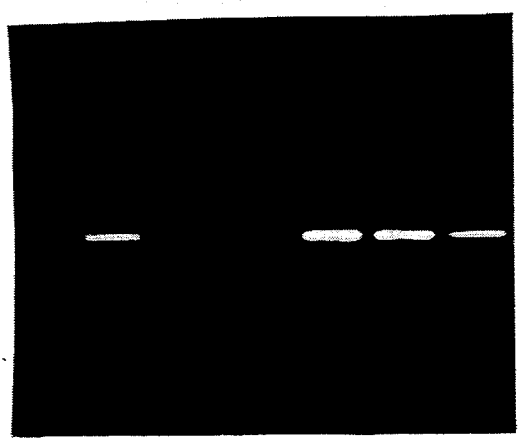
<-- 2 KB product size FIG.4A   2 min. 98° C, 10 min. 65° C, 20 cycles
| λH3 std | AT | | KT-278 | | ST | | KT-291 | | λH3 std |
|---|---|---|---|---|---|---|---|---|---|
| | 3/4 | 3/8 | 1/4 | 1/8 | 3 | 1.5 | 1/4 | 1/8 | |
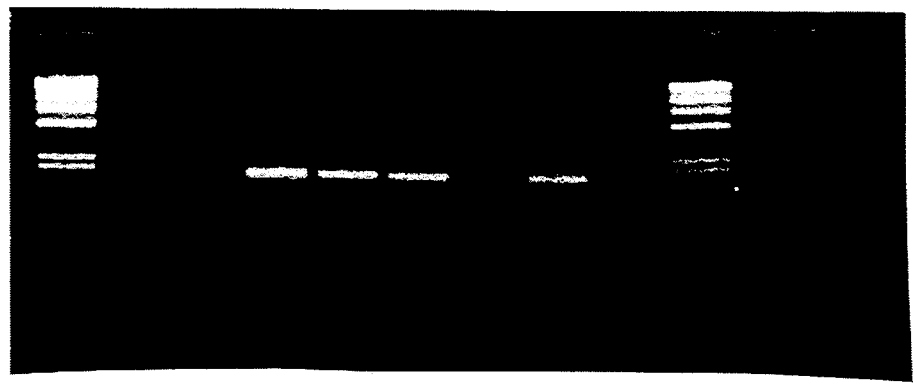
FIG.4B   2 min. 95° C, 10 min. 65° C, 20 cycles
| λH3 std | AT | | KT-278 | | ST | | KT-291 | | λH3 std |
|---|---|---|---|---|---|---|---|---|---|
| | 3/4 | 3/8 | 1/4 | 1/8 | 3 | 1.5 | 1/4 | 1/8 | |

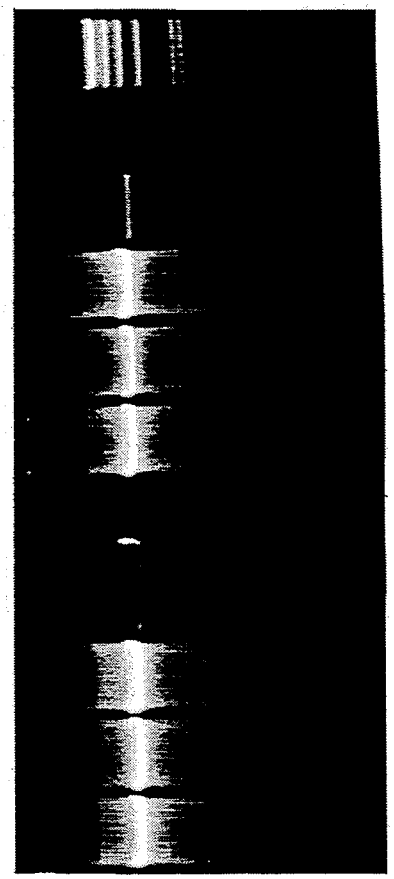

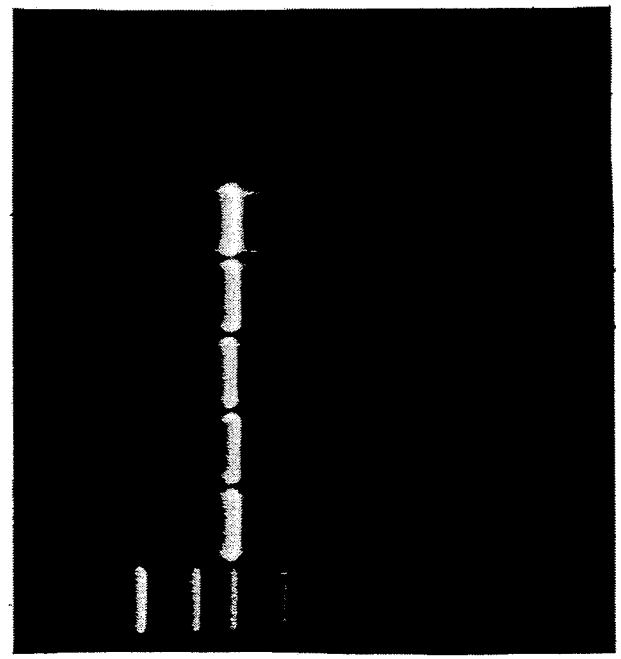

20 cycles of 2 min. 95°, 1 min. 60°, 30 min. 72° ul of KlenTaq-278    1    1    1    1    1
ul of Pfu DNA Pol    1   1/4  1/16 1/64  0

| Channel: | 1 | 2 | 3 | 4 | 5 | 6 | 7 | 8 |
|---|---|---|---|---|---|---|---|---|
| Template DNA: | λplac5 | λpcytT | λpcytT | λplac5 | λplac5 | λK138 | λK138 | λK138 |
| ng of template: | 1 | 1 | 10 | 1 | 10 | 1 | 10 | 10 |
| primer 1 SEQ ID NO: | 9 | 7 | 7 | 10 | 10 | 7 | 7 | 9 |
| primer 2 SEQ ID NO: | 8 | 8 | 8 | 8 | 8 | 8 | 8 | 8 |
| Size of PCR product Expected, in kb: | 8.4 | 12.5 | 12.5 | 15 | 15 | 18 | 18 | 19.7 |

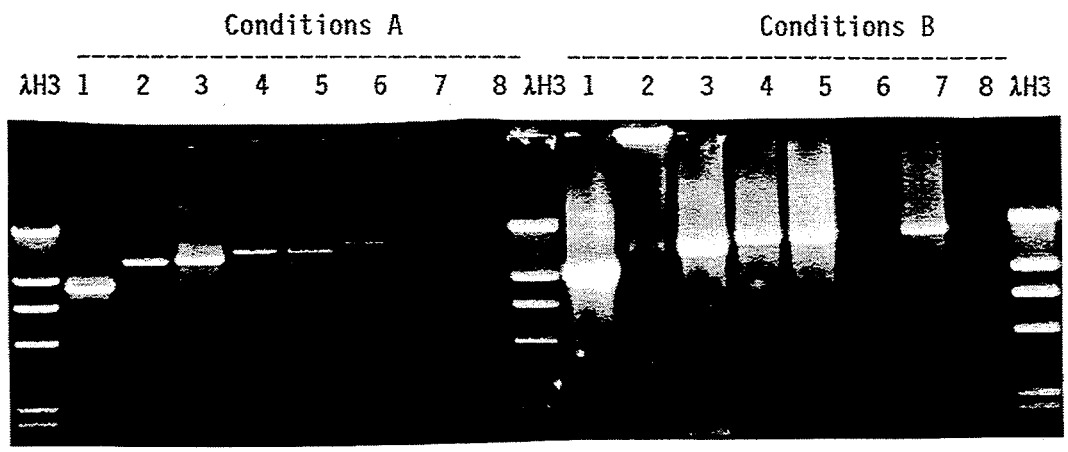

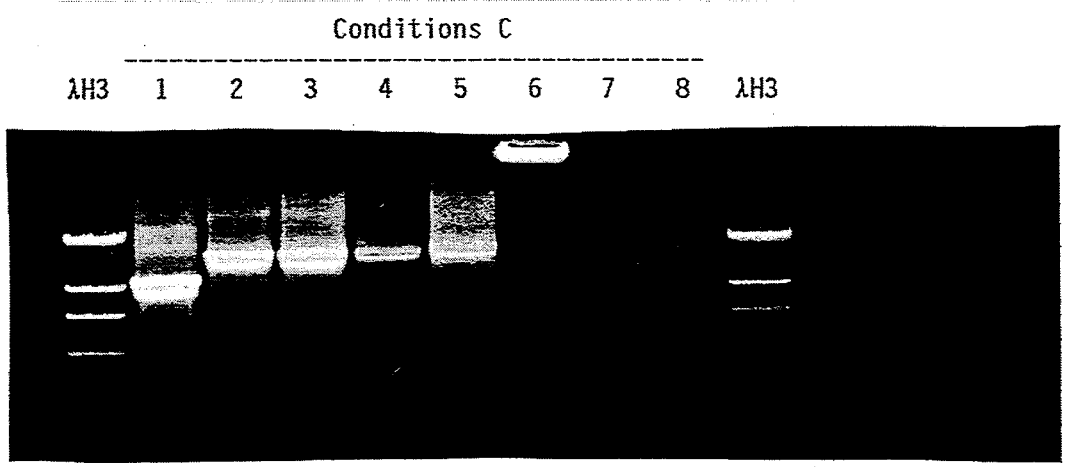

PCR Cycling Conditions A: 2 seconds 94°, 11 minutes 70°, 20 cycles.
PCR Cycling Conditions B: 2 seconds 94°, 11 minutes 70°, 30 cycles.
PCR Cycling Conditions C: 2 seconds 93°, 11 minutes 70°, 30 cycles.

λplac5 is a lambda transducing phage carrying the lacZ gene. λpcytT is a λEMBL4-vectored clone of the cytotoxin gene region of Helicobacter pylori DNA. λK138 is a λEMBL4-vectored clone of E. coli DNA spanning the lac operon.

λH3 size standards visible are 23130, 9416, 6557, 4361, 2322, and 2027 bp.

THERMOSTABLE DNA POLYMERASE WITH ENHANCED THERMOSTABILITY AND ENHANCED LENGTH AND EFFICIENCY OF PRIMER EXTENSION

BACKGROUND OF THE INVENTION

The present invention is directed to DNA polymerases, and more particularly, to a novel mutation of *Thermus aquaticus* and *Thermus flavus* DNA polymerases exhibiting enhanced thermostability over any form of these enzymes now known. The invention is also directed to recombinant DNA sequences encoding such DNA polymerases, and vector plasmids and host cells suitable for the expression of these recombinant DNA sequences. The invention is also directed to a novel formulation of the DNA polymerases of the present invention and other thermostable DNA polymerases, which formulation of enzymes is capable of efficiently catalyzing the amplification by PCR (the polymerase chain reaction) of unusually long and faithful products.

DNA polymerase obtained from the hot springs bacterium *Thermus aquaticus* (Taq DNA polymerase) has been demonstrated to be quite useful in amplification of DNA, in DNA sequencing, and in related DNA primer extension techniques because it is thermostable. Thermostable is defined herein as having the ability to withstand temperatures up to 95° C. for many minutes without becoming irreversibly denatured, and the ability to polymerize DNA at high temperatures (60° to 75° C.). The DNA and amino acid sequences described by Lawyer et al., J. Biol. Chem. 264:6427 (1989), GenBank Accession No. J04639, define the gene encoding *Thermus aquaticus* DNA polymerase and the enzyme *Thermus aquaticus* DNA polymerase as those terms are used in this application. The highly similar DNA polymerase (Tfl DNA polymerase) expressed by the closely related bacterium *Thermus flavus* is defined by the DNA and amino acid sequences described by Akhmetzjanov, A. A., and Vakhitov, V. A. (1992) Nucleic Acids Research 20:5839, GenBank Accession No. X66105. These enzymes are representative of a family of DNA polymerases, also including *Thermus thermophilus* DNA polymerase, which are thermostable. These enzymes lack a 3-exonuclease activity such as that which is effective for editing purposes in DNA polymerases such as *E. coli* DNA polymerase I, and phages T7, T3, and T4 DNA polymerases.

Gelfand et al., U.S. Pat. No. 4,889,818 describe a wild-type (abbreviation used here: WT), native *Thermus aquaticus* DNA polymerase. Gelland et al., U.S. Pat. No. 5,079,352 describe a recombinant DNA sequence which encodes a mutein of *Thermus aquaticus* DNA polymerase from which the N-terminal 289 amino acids of *Thermus aquaticus* DNA polymerase have been deleted (claim 3 of '352, commercial name Stoffel Fragment, abbreviation used here: ST), and a recombinant DNA sequence which encodes a mutein of *Thermus aquaticus* DNA polymerase from which the N-terminal 3 amino acids of *Thermus aquaticus* DNA polymerase have been deleted (claim 4 of '352, trade name AmpliTaq, abbreviation used here: AT). Gelland et al. report their muteins to be "fully active" in assays for DNA polymerase, but data as to their maximum thermostability is not presented.

The development of other enzymatically active mutein derivatives of *Thermus aquaticus* DNA polymerase is hampered, however, by the unpredictability of the impact of any particular modification on the structural and functional characteristics of the protein. Many factors, including potential disruption of critical bonding and folding patterns, must be considered in modifying an enzyme and the DNA for its expression. A significant problem associated with the creation of N-terminal deletion muteins of high-temperature *Thermus aquaticus* DNA polymerase is the prospect that the amino-terminus of the new protein may become wildly disordered in the higher temperature ranges, causing unfavorable interactions with the catalytic domain(s) of the protein, and resulting in denaturation. In fact, a few deletions have been constructed which appear to leave the identifiable domain for DNA polymerase intact, yet none of these deletions have thermostability at temperatures as high as 99° C.

While *Thermus aquaticus* DNA polymerase has shown remarkable thermostability at much higher temperatures than that exhibited by other DNA polymerases, it loses enzymatic activity when exposed to temperatures above 95°–97° C. Moreover, its fidelity at 72° C. (the recommended temperature for DNA synthesis) is limited to an effective error rate of approximately 1/9000 bp. Gelland et al.'s mutein ST of *Thermus aquaticus* DNA polymerase (with an N-terminal 289 a.a. deletion) is significantly more stable than AT, but ST exhibits significantly decreased activity when cycled to 98° C., and much less, if any, activity when cycled to 99° C., during the denaturation phase of PCR cycles.

Kainze et al. (Analytical Biochem. 202:46–49(1992) report a PCR amplification of over 10 kb: a 10.9 kb and a 15.6 kb product, utilizing an enzyme of unpublished biological source (commercially available as "Hot Tub" DNA polymerase). Kainze et al. report achieving a barely visible band at 15.6 kb after 30 cycles, starting with 1 ng of λ DNA template per 100 ul of reaction volume. The efficiency of this amplification was shown to be relatively low, although a quantitative calculation of the efficiency was not presented, Attempts by Kainze et al. to make WT *Thermus aquaticus* DNA polymerase perform in the 10–15 kb size range were not successful, nor have successful results been reported by anyone else for any form of *Thermus aquaticus* DNA polymerase in this size range. There is no report of any longer DNA products amplifiable by PCR.

A DNA polymerase which retains its thermostability at 98° or 99° C. would allow more efficient and convenient DNA analysis in several situations including "colony PCR" (see FIG. 5), and/or allow thermal cycler overshoot without inactivation of the enzyme activity. A thermostable DNA polymerase or DNA polymerase formulation which exhibits improved fidelity relative to AT or WT *Thermus aquaticus* DNA polymerase at optimum temperatures for synthesis would be highly desirable for applications in which the target and product DNA is to be expressed rather than merely detected. The PCR amplification method is currently limited by two factors: The length of the products obtainable, and the fidelity of those products. A thermostable DNA polymerase preparation capable of efficient amplification of DNA spans in excess of 6 kb would significantly expand the scope of applications of PCR. For instance, whole plasmids, and constructs the size of whole plasmids, could be prepared with this method, which would be especially valuable in cases in which a portion of the DNA in question is toxic or incompatible with plasmid replication when introduced into *E. coli*. If this thermostable DNA polymerase preparation simultaneously conferred increased fidelity to the PCR amplification, the resulting large products would be much more accurate, active and/or valuable in research and applications, especially in situations involving expression of the amplified sequence. If the thermostable DNA polymerase preparation allowed, in addition, more highly concentrated yields of pure product, this would enhance the method of PCR to the point where it could be used more effectively to replace plasmid replication as a means to produce desired DNA fragments in quantity.

SUMMARY OF THE INVENTION

Among the several objects of the invention, therefore, may be noted the provision of a DNA polymerase which can survive meaningful repeated exposure to temperatures of 99° C.; the provision of a highly thermostable DNA polymerase which exhibits greater fidelity than *Thermus aquaticus* DNA polymerase when utilized at standard *Thermus aquaticus* DNA polymerase extension reaction temperatures; the provision of such a DNA polymerase which is useful for PCR amplification techniques from DNA templates and from single colonies of *E. coli*, single-stranded (linear) amplification of DNA, nucleic acid sequencing, DNA restriction digest filling, DNA labelling, in vivo footprinting, and primer-directed mutagenesis. Further objects of the invention include the provision of recombinant DNA sequences, vectors and host cells which provide for the expression of such DNA polymerase.

Additional objects include the provision of a formulation of thermostable DNA polymerases capable of efficiently catalyzing primer extension products of greater length than permitted by conventional formulations, and that reduces the mutagenicity generated by the PCR process, without significant sacrifice in flexibility, specificity, and efficiency; and the provision of an improved process for amplification by PCR which can be utilized to reliably synthesize nucleic acid sequences of greater length.

Briefly, therefore, the present invention is directed to a novel, recombinant DNA sequence encoding a DNA polymerase having an amino acid sequence comprising substantially the same amino acid sequence as the *Thermus aquaticus* or *Thermus flavus* DNA polymerase, excluding however the N-terminal 280 amino acid residues of WT *Thermus aquaticus* or the N-terminal 279 amino acids of *Thermus flavus* DNA polymerase. The present invention is further directed to a vector comprising the above recombinant DNA sequences and host cells containing such vectors.

Additionally, the present invention is directed to a DNA polymerase having an amino acid sequence comprising substantially the same amino acid sequence of the *Thermus aquaticus* or *Thermus flavus* DNA polymerase, but lacking the N-terminal 280 amino acid residues of *Thermus aquaticus* DNA polymerase, or the N-terminal 279 amino acids of *Thermus flavus* DNA polymerase.

In a further embodiment, the present invention is directed to a novel formulation of thermostable DNA polymerases, including a majority component comprised of at least one thermostable DNA polymerase lacking 3'-exonuclease activity and a minority component comprised of at least one thermostable DNA polymerase exhibiting a 3'-(editing) exonuclease activity.

The invention is further directed to an improvement in a process for amplification of nucleic acid sequences by PCR wherein the improvement comprises mixing together a majority component comprised of at least one thermostable DNA polymerase lacking 3'-exonuclease activity and a minority component consisting of at least one thermostable DNA polymerase exhibiting 3'-exonuclease activity. The formulation thereby created is used to catalyze primer extension during the PCR process, thus extending the applicable size range for efficient PCR amplification.

Other objects and features will be in part apparent and in part pointed out hereinafter.

SUMMARY OF ABBREVIATIONS

The listed abbreviations, as used herein, are defined as follows:
Abbreviations:
bp=base pairs
kb=kilobase; 1000 base pairs
nt=nucleotides
BME=beta-mercaptoethanol
$PP_i$=sodium pyrophosphate
Pfu=*Pyrococcus furiosus*
Taq=*Thermus aquaticus*
Tfl=*Thermus flavus*
Klentaq-nnn=N-terminally deleted *Thermus aquaticus* DNA polymerase that starts with codon nnn+1, although that start codon and the next codon may not match the WT sequence because of alterations to the DNA sequence to produce a convenient restriction site.
WT=wild-type (full length) or deletion of only 3 aa
aa=amino acid(s)
ST=Stoffel fragment, an N-terminal deletion of *Thermus aquaticus* DNA polymerase that could be named Klentaq-288.
-LA=Long and Accurate; an unbalanced mixture of two DNA polymerases.
PCR=(noun) 1. The Polymerase Chain Reaction.
2. One such reaction/amplification experiment.
(verb) To amplify via the polymerase chain reaction.
ul=microliter(s)
ATCC=American Type Culture Collection

BRIEF DESCRIPTION OF THE DRAWINGS

FIG. 1A & 1B depict the nucleotide sequence of primers that can be used for amplification of the gene for a preferred embodiment of the DNA polymerase of this invention. The bulk of the DNA sequence for the gene (between the primers) and the resultant amino acid sequence of the enzyme, is defined by the indicated Gen Bank entry.

FIG. 2 depicts the nucleotide sequence of the same primers as in FIG. 1, and shows that these same primers can be used for amplification of the analogous gene from *Thermus flavus*.

FIG. 3 is a photograph of an agarose gel depicting a PCR amplification reaction conducted using the prior art enzyme *Thermus aquaticus* DNA polymerase (AmpliTaq; AT) and a preferred embodiment of the DNA polymerase of this invention, tested with differing peak denaturation temperatures lasting a full 2 min each for 20 cycles. Full activity at 98° and partial but useful activity at 99° is exhibited by the preferred embodiment of this invention, whilst AT is unable to withstand these temperatures. FIG. 3 demonstrates that the enzyme of the present invention is more thermostable than AT in a practical test—PCR amplification.

FIG. 4A & 4B are photographs of an agarose gel depicting a PCR amplification reaction conducted using 4 enzymes: the prior art enzyme *Thermus aquaticus* DNA polymerase (AmpliTaq; AT); the DNA polymerase of this invention (KlenTaq-278); the prior art enzyme AmpliTaq Stoffel Fragment (ST); and KlenTaq-291. All were tested with PCR denaturation steps carried out at 95° C. (control standard temperature), and at 98° C. All were tested at two levels of enzyme, the lower level being as close as practicable to the minimum necessary to support the reaction at the control temperature.

Note that both KlenTaq-291 and ST behave identically, losing most, but not all, of their activity when used at 98° C., yet KlenTaq-278 is at least twice as able to withstand use of the higher denaturation temperature, AT is seen to be drastically reduced in effectiveness by exposure to 98° C., The behaviour of these enzymes is reproducible except for ST, which is at its best in the presented experiment, but performs more poorly when used in the amounts recommended by the manufacturer.

Figure 5:
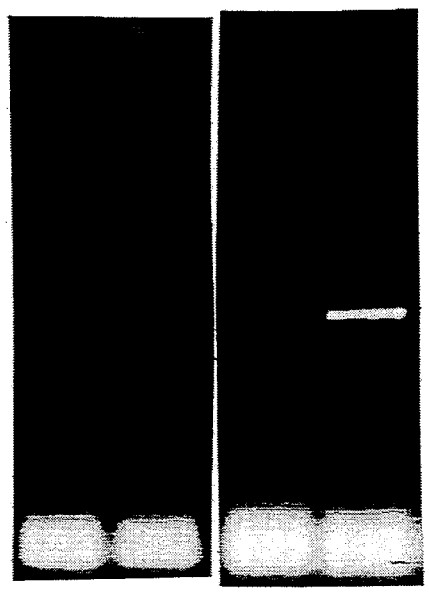

FIG. 5 is a photograph of an agarose gel analysis of the products of colony PCR carried out at the standard peak denaturation temperature of 95° C. compared to the newly available temperature of 98° C. allowed by the enzyme of the present invention. FIG. 5 demonstrates an application advantage of the use of the newly available peak denaturation temperature.

Figure 6C:
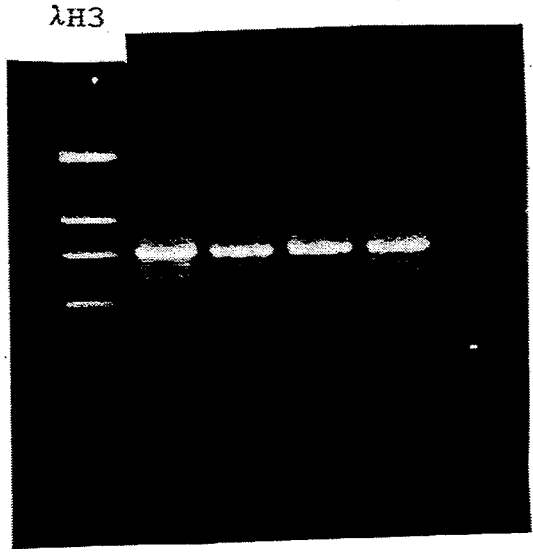

FIG. 6A, 6B and 6C are a series of three photographs, each Of an agarose gel on which was loaded a portion of a test PCR experiment. FIG. 6 demonstrates the large increase in efficiency of large DNA span PCR achieved by variations of a preferred embodiment of the enzyme formulation of the invention. Although KlenTaq-278 or Pfu DNA polymerase, alone, are shown to catalyze a low level of 6.6 kb PCR product formation, various combinations of the two are seen to be much more efficient. Lower and lower amounts of Pfu are seen to be effective, down to the minimum presented, 1/640.

FIG. 7 is a photograph of an agarose gel on which were analyzed the products of PCR experiments to test the performance of an embodiment of the invention in catalyzing the amplification of fragments even longer than 6.6 kb. FIG. 7 demonstrates the ability to amplify 8.4 kb, 12.5 kb, 15 kb, and 18 kb with high efficiency and large yield, utiliziing the 1/640 ratio embodiment of the enzyme formulation of the invention.

Figure 8:
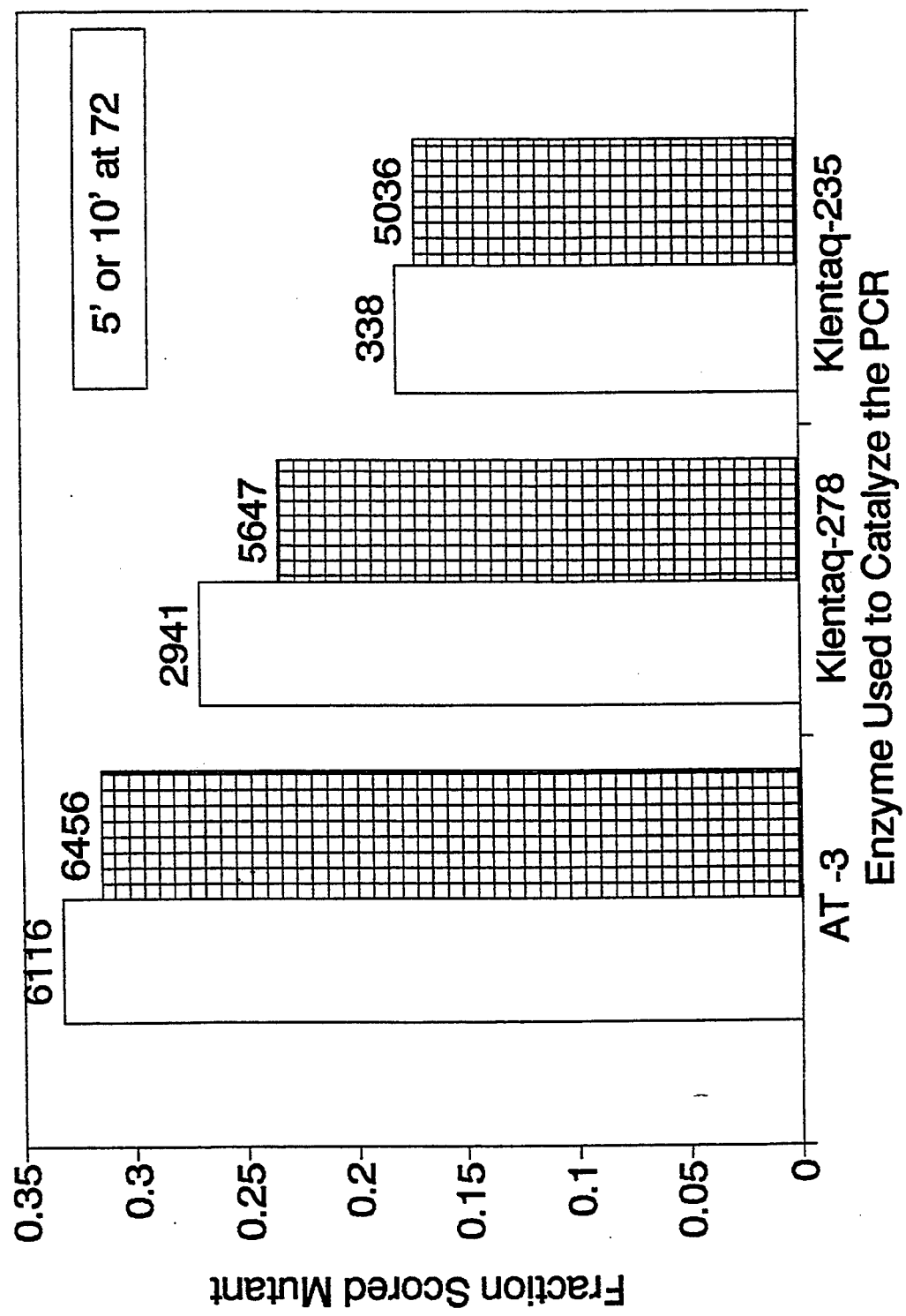

FIG. 8 is a bar graph enumerating the differences in the number of mutations introduced into a PCR product, the lacZ gene, by the near full-length prior art −3 deletion of *Thermus aquaticus* DNA polymerase, compared to the number of mutations introduced by Klentaq-278.

DESCRIPTION OF THE PREFERRED EMBODIMENT

Referring now to FIG. 1, the amplification by PCR of the recombinant DNA sequence encoding a preferred embodiment of the DNA polymerase of the invention (referred to herein as Klentaq-278), is set forth. As depicted in FIG. 1, an initiator methionine and a glycine residue occupy the first two N-terminal positions of Klentaq-278, previously occupied by residues 279 and 280 of WT *Thermus aquaticus* DNA polymerase, followed by the amino acid sequence of wild-type *Thermus aquaticus* DNA polymerase, beginning with the amino acid residue at position 281 as described by Lawyer et al. The codons encoding amino acid residues 1 through 280 of *Thermus aquaticus* DNA polymerase are therefore deleted, and the amino acids 1 thru 280 are not present in the resulting gene product. Another preferred embodiment of the DNA polymerase of the invention is depicted in FIG. 2. In this embodiment, the same deletion mutation described above is made to the highly analogous enzyme *Thermus flavus* DNA polymerase.

It will be appreciated that minor variations incorporated into the DNA encoding for, or the amino acid sequence as described herein, which retain substantially the amino acid sequence as set forth above, and which do not significantly affect the thermostability of the polymerase are included within the scope of the invention.

Surprisingly, the mutant DNA polymerase Klentaq-278 exhibits thermostability at temperatures above those reported for any previous variant of *Thermus aquaticus* DNA polymerase and has demonstrated a fidelity in final PCR products which is greater than that of WT *Thermus aquaticus* DNA polymerase, when both are utilized at the 72° C. temperatures recommended for DNA synthesis. Further, since Klentaq-278 does not have the 5'-exonuclease activity associated with *Thermus aquaticus* DNA polymerase (removed as a consequence of the N-terminal deletion), it is significantly superior to wild-type *Thermus aquaticus* DNA polymerase for DNA sequencing. Mutagenesis results, and mismatched matched primer testing, suggest that Klentaq-278 is less processive and is less likely to extend a mispaired base than wild-type *Thermus aquaticus* DNA polymerase.

Thermostability tests with Klentaq-278, Stoffel Fragment (ST, alternative designation, Klentaq-288) and Klentaq-291 have been carried out, The test used involves 20 PCR cycles with a full 2 minutes each at the peak test temperature, such as 97° C., 98° C., or 99° C., and the intensity of the resulting amplified bands is compared to 2 minutes at 97° C., or at a lower control denaturation temperature, such as 95° C. (at which all of these variants are stable), These data indicate that ST and Klentaq-291 behave similarly, having thermostability at 98° C. that is similar to each other yet distinct from Klentaq-278, which exhibits little detectable thermolability at 98° C. in these tests. These data suggest that the number of N-terminal amino acids is important to the enhanced thermostability exhibited by the DNA polymerase of the invention.—Evidently deletions ST and Klentaq-291 are in a class which has removed too many amino acids (10 more and 13 more) for the optimum stability demonstrated by the invention Klentaq-278.

The DNA polymerase from the bacterium sometimes designated *Thermus fiavus* (and sometimes *Thermus aquaticus*—see ATCC catalog) is highly homologous to the WT *Thermus aquaticus* DNA polymerase. In the region of the deletions being discussed here, the enzymes and genes are exactly homologous, and it is believed that the differences between the pair ST, Klentaq-291 and the superior Klentaq-278 would remain if the analogous deletions were constructed. Indeed, the primers in FIG. 2 could be used on *Thermus fiavus* DNA to construct KlenTfi-277 in exactly the manner described here for the construction and isolation of Klentaq-278. The *Thermus flavus* DNA polymerase -277 enzyme and variations thereof which exhibit similar thermostability are therefore also within the scope of this invention.

The invention also features a vector which includes a recombinant DNA sequence encoding a DNA polymerase comprising the amino acid sequence of *Thermus aquaticus* or *Thermus flavus* DNA polymerase, except that it adds a methionine and glycine residue at the N-terminal and excludes the N-terminal 280 amino acids of wild-type *Thermus aquaticus* DNA polymerase (see Lawyer et al., supra).

In preferred embodiments, the vector is that nucleic acid present as plasmid pWB254b (SEQ ID NO:5) deposited as ATCC No. 69244 or a host cell containing such a vector.

In a related aspect, the invention features a purified DNA polymerase having an amino acid sequence as discussed above. As used herein, "purified" means that the polymerase of the invention is isolated from a majority of host cell proteins normally associated with it. Preferably, the polymerase is at least 10% (w/w) of the protein of a preparation. Even more preferably, it is provided as a homogeneous preparation, e.g., a homogeneous solution.

In general, the recombinant DNA sequence of the present invention is amplified from a *Thermus aquaticus* genomic DNA or from a clone of the portion of the *Thermus aquaticus* DNA polymerase gene which is larger than the desired span, using the polymerase chain reaction (PCR, Saiki et al., Science 239:487, 1988), employing primers such as those in FIG. 2 into which appropriate restriction sites have been incorporated for subsequent digestion.

The recombinant DNA sequence is then cloned into an expression vector using procedures well known to those in this art. Specific nucleotide sequences in the vector are cleaved by site-specific restriction enzymes such as NcoI and HindIII. Then, after optional alkaline phosphatase treatment of the vector, the vector and target fragment are ligated together with the resulting insertion of the target codons in place adjacent to desired control and expression sequences. The particular vector employed will depend in part on the type of host cell chosen for use in gene expression. Typically, a host-compatible plasmid will be used containing genes for markers such as ampicillin or tetracycline resistance, and also containing suitable promoter and terminator sequences.

In a preferred procedure, the recombinant DNA expression sequence of the present invention is cloned into plasmid pWB253 (expresses KlenTaq-235 deposited as ATCC No. 68431) or pWB250 (expresses luciferase/NPTII fusion), the backbone of which is pTAC2 (J. Majors, Washington University), a pBR322 derivative. The specific sequence of the resulting plasmid, designated pWB254b is SEQ ID NO:5.

Bacteria, e.g., various strains of *E. coli*, and yeast, e.g., Baker's yeast, are most frequently used as host cells for expression of DNA polymerase, although techniques for using more complex cells are known. See, e.g., procedures for using plant cells described by Depicker, A., et al., *J. Mol. Appl. Gen.* (1982) 1:561. *E. coli* host strain X7029, wild-type F−, having deletion X74 covering the lac operon is utilized in a preferred embodiment of the present invention.

A host cell is transformed using a protocol designed specifically for the particular host cell. For *E. coli*, a calcium treatment, Cohen, S. N., Proc. Natl. Acad. Sci. 69:2110 (1972), produces the transformation. Alternatively and more efficiently, electroporation of salt-free *E. coli* is performed after the method of Dower et al. (1988), Nucleic Acids Research 16:6127–6145. After transformation, the transformed hosts are selected from other bacteria based on characteristics acquired from the expression vector, such as ampicilin resistance, and then the transformed colonies of bacteria are further screened for the ability to give rise to high levels of isopropylthiogalactoside (IPTG)-induced thermostable DNA polymerase activity. Colonies of transformed *E. coli* are then grown in large quantity and expression of Klentaq-278 DNA polymerase is induced for isolation and purification.

Although a variety of purification techniques are known, all involve the steps of disruption of the *E. coli* cells, inactivation and removal of native proteins and precipitation of nucleic acids. The DNA polymerase is separated by taking advantage of such characteristics as its weight (centrifugation), size (dialysis, gel-filtration chromatography), or charge (ion-exchange chromatography). Generally, combinations of these techniques are employed together in the purification process. In a preferred process for purifying Klentaq-278 the *E. coli* cells are weakened using lysozyme and the cells are lysed and nearly all native proteins are denatured by heating the cell suspension rapidly to 80° C. and incubating at 80°–81° C. for 20 minutes. The suspension is then cooled and centrifuged to precipitate the denatured proteins. The supernatant (containing Klentaq-278) then undergoes a high-salt polyethylene-imine treatment to precipitate nucleic acids. Centrifugation of the extract removes the nucleic acids and Klentaq-278 is concentrated by use of ammonium sulfate precipitation before chromatography, preferably on a heparin-agarose column. More detail of the isolation is set forth below in Example 3.

The novel DNA polymerase of the present invention may be used in any process for which such an enzyme may be advantageously employed. In particular, this enzyme is useful for PCR amplification techniques, nucleic acid sequencing, cycle sequencing, DNA restriction digests, DNA labelling, in vivo DNA footprinting, and primer-directed mutagenesis.

Amplification

Polymerase chain reaction (PCR) is a method for rapidly amplifying specific segments of DNA, in geometric progression, up to a million fold or more. See, e.g., Mullis U.S. Pat. No. 4,683,202. which is incorporated herein by reference. The technique relies on repeated cycles of DNA polymerase-catalyzed extension from a pair of primers with homology to the 5' end and to the complement of the 3' end of the DNA segment to be amplified. A key step in the process is the heat denaturing of the DNA primer extension products from their templates to permit another round of amplification. The operable temperature range for the denaturing step generally ranges from about 93° C. to about 95° C., which irreversibly denatures most DNA polymerases, necessitating the addition of more polymerase after each denaturation cycle. However, no additional DNA polymerase needs to be added if thermostable DNA polymerases such as *Thermus aquaticus* DNA polymerase are used, since they are able to retain their activity at temperatures which denature double-stranded nucleic acids. As described in Example 4, below. Klentaq-278 has demonstrated the ability to survive meaningful repeated exposure to temperatures of 99° C. higher than for any previously known DNA polymerase.

Klentaq-278 has also been demonstrated to have a higher fidelity than wild-type *Thermus aquaticus* DNA polymerase at 72° C., the recommended synthesis temperature. The data for this has been gathered by a method involving the PCR amplification of a lacZ DNA gene flanked by two selectable markers [Barnes, W. M. (1992) Gene 112, 29–25. Representative data comparing the preferred embodiment of this invention Klentaq-278 to AT and another analogous N-terminal deletion, Klentaq-235, is shown in FIG. 8, which demonstrates that different N-terminal deletions reproducibly exhibit differing fidelities as measured in the final PCR product.

Similar fidelity data for the enzyme ST is not available, since it is difficult for the commercial preparation of this enzyme to catalyze PCR of the long test fragment (4.8 kb) used for this assay. It is not yet known whether the difficulty with ST for these experiments is caused merely by formulation (its concentration is less, such that 10–15 times more volume is necessary for a 2 kb PCR amplification, and for these deletions more enzyme is needed for longer target DNAs), or whether ST may be intrinsically unable to catalyze such a long-target PCR amplification.

DNA Sequencing

Particular DNA sequences may be elucidated by the Sanger Method (Sanger, F., Nicklen, S. and Coulson, A. R., DNA sequencing with chain-terminating inhibitors, Proc. Nat. Acad. Sci. USA, 74 (1977) 5463–5467), using dideoxy analogs. DNA polymerases are used in these methods to catalyze the extension of the nucleic acid chains. However, in its natural form, *Thermus aquaticus* DNA polymerase (like many other polymerases) includes a domain for 5'-exonuclease activity. This associated exonuclease activity can, under certain conditions including the presence of a slight excess of enzyme or if excess incubation time is employed, remove 1 to 3 nucleotides from the 5' end of the sequencing primer, causing each band in an alpha-labelled sequencing gel to appear more or less as a multiplier. If the label of the sequencing gel is 5', the exonuclease would not be able to cause multipliers, but it would instead reduce the signal. As a result of the deletion of the N-terminal 280 amino acid residues of *Thermus aquaticus* DNA polymerase, Klentaq-278 has no exonuclease activity and it avoids the sequencing hazards caused by 5'-exonuclease activity. Klentaq-278 can be used effectively in thermostable DNA polymerase DNA sequencing. There are basically two types of dideoxy DNA sequencing that Klentaq-278 is good for—original dideoxy (Sanger et al. supra; Innis et al., Proc. Natl. Acad. Sci. USA 85:9436, 1988)and cycle sequencing.

Innis et al. describe a good procedure for dideoxy sequencing, but when the WT *Thermus aquaticus* DNA polymerase is used this procedure is prone to doubled or tripled bands on the sequencing gel, as demonstrated in the patent application Ser. No. 07/594,637 which should be available to the examiner and which is incorporated herein by reference. Klentaq-278 is as effective in curing this problem as the subject of that patent application, Klentaq-235, a.k.a. DeltaTaq.

The procedure recommended for original-type (non-cycled, Innis et al.) dideoxy sequencing with Klentaq-278 is that in the USB Taquence 2.0 dideoxy sequencing kit, a copy of which is appended to this application (Appendix 1).

The procedure recommended for cycle sequencing is that in the USB Cycle Sequencing Kit. A copy of this procedure is appended to this application (Appendix 2).

Other Uses

Klentaq-278 has also been used successfully for primer-directed mutagenesis, in vivo footprinting, DNA labelling and for preparation of non-sticky Lambda DNA fragment size standards. These procedures are discussed below.

Klentaq-278, especially in the formulation Klentaq-LA (discussed below), can be used to extend site-specific mutagenic primer(s) which are annealled to single-stranded templates. It substitutes for Klenow enzyme (the large fragment of *E. coil* DNA polymerase I) and T7 DNA polymerase in this process, showing more primer selectivity at 60°–65° C. than Klenow enzyme at 37° C., and working to completion or sufficient incorporation in 12 mins., as compared to the one hour or more required for Klenow enzyme.

Klentaq-278 has also been shown to be useful (and superior to wild-type *Thermus aquaticus* DNA polymerase) for the post-PCR labelling steps with the third (second nested) primer in ligase-mediated, PCR-assisted, in vivo footprinting, I am indebted to I. Ghattas, Washington University, St. Louis, Mo. for this information. These studies are similar to those of Garritty & Wold (Garrity, P. A., and Wold, B. J. (1992) Effects of different DNA polymerases in ligation-mediated PCR: enhanced genomic sequencing and in vivo footprinting. Proc Natl Acad Sci USA 89, 1021–1025)

Klentaq-278 is also useful for DNA labelling. For random primers, a length of at least 9 nt is recommended, and preferably the reaction is warmed slowly (over 20–30 mins.) from 37° to 65° C. Most preferably, a programmable heat block, using procedures well-known to those in this art, is utilized for the DNA labelling.

Another use of Klentaq-278 is for the preparation of Lambda DNA restriction digests that do not have the sticky ends partially stuck together. As a result of including Klentaq-278 and the four DNA dNTPs in with a HindIII digest performed at 55° C., bands 1 and 4 are not partially attached to each other.

Deposit

Strain pWB254b/X7029 was deposited with the American Type Culture Collection, Maryland, on Feb. 18, 1993 and assigned the number ATCC No. 69244. Applicant acknowledges his responsibility to replace this culture should it die before the end of the term of a patent issued hereon, 5 years after the last request for a culture, or 30 years, whichever is the longer, and its responsibility to notify the depository of the issuance of such a patent, at which time the deposits will be made available to the public. Until that time the deposits will be made available to the Commissioner of Patents under the terms of 37 C.F.R. Section 1–14 and 35 U.S.C. §112.

The following examples illustrate the invention.

EXAMPLE 1

Construction of an Expressible Gene for Klentaq-278

In order to construct the Klentaq-278 DNA polymerase gene having a recombinant DNA sequence shown as the nucleotide sequence of FIG. 1, the following procedure was followed.

The mutated gene was amplified from 0.25 ug of total *Thermus aquaticus* DNA using the polymerase chain reaction (PCR, Saiki et al., Science 239:487, 1988) primed by the two synthetic DNA primers of FIG. 1. Primer KT1, SEQ ID NO:1, has homology to the wild-type DNA starting at codon 280; this primer is designed to incorporate a NcoI site into the product amplified DNA. Primer Klentaq32, SEQ ID NO:3, a 33mer spanning the stop codon on the other strand of the wild-type gene encoding *Thermus aquaticus* DNA polymerase, and incorporating a HindIII site and a double stop codon into the product DNA.

The buffer for the PCR reaction was 20 mM Tris HCl pH 8.55, 2.5 mM $MgCl_2$, 16 mM $(NH_4)_2SO_4$, 150 ug/ml BSA, and 200 uM each dNTP. The cycle parameters were 2' 95°, 2' 65°, 5' 72°.

In order to minimize the mutations introduced by PCR (Saiki et al., supra), only 16 cycles of PCR were performed before phenol extraction, ethanol precipitation, and digestion with the restriction enzymes NcoI and HindIII,

EXAMPLE 2

Preparation of an Expression Vector

The product NcoI and HindIII fragment was cloned into plasmid pWB254b which had been digested with NcoI, HindIII, and calf intestine alkaline phosphatase. The, backbone of this plasmid, previously designated pTAC2 and obtained from J. Majors, carries the following elements in counter-clockwise direction from the PvuII site of pBR322 (an apostrophe ' designates that the direction of expression is clockwise instead of counter clockwise): a partial lacZ' sequence, lacI', lac-PUV5 (orientation not known), two copies of the tac promoter from PL Biochemicals Pharmacia-LKB; catalog no. 27-4883), the T7 gene 10 promoter and start codon modified to consist of a NcoI site, a HindIII site, the trpA terminator (PL no. 27-4884-01), an M13 origin of replication, and the $Amp^R$ gene of pBR322. Expression of the cloned gene is expected to be induced by 0.1 mM IPTG.

Ampicillin-resistant colonies arising from the cloning were assayed by the single colony thermostable DNA polymerase assay of Sanger et al. (1991) [GENE 97:119–231 and 4 strong positives were sized by the toothpick assay (Barnes, Science 195:393, 1977). One of these, number 254.7, was of the expected size except for a small proportion of double insert. This plasmid was further purified by electroporation into *E. coli* X7029 and screened for size by the toothpick assay, and one plasmid of the expected size with no double insert contamination was designated pWB254b. This plasmid was used for the production of Klentaq-278 described herein.

EXAMPLE 3

Purification of Large Amounts of Klentaq-278

Plasmid pWB254 has a double (tandem repeat) tac promoter and the T7 gene 10 leader sequence, an ATG start codon, a glycine codon and then codons 280–832 of *Thermus aquaticus* DNA polymerase, then a tandem pair of stop codons followed by the trp transcription terminator. The pBR322-based plasmid vector (pTac2 from John Majors) is ampicillin resistant. The cells are grown on very rich medium (see below). Bacterial host X7029 is wild-type F−*E. coli* except for deletion X74 of the lac operon.

Medium: Per liter water, 100 mg ticarcillin (added when cool), 10 g Y.E., 25 g. Tryprone, 10 g. glucose, 1XM9 salts with no NaCl (42 mM $Na_2PO_4$, 22 mM $KH_2PO_4$, 19 mM $NH_4Cl$). Do not autoclave the glucose and the 10XM9 together; instead, autoclave one of them separately and mix in later. Adjust pH to 8 with 5M NaOH (about 1 ml).

Add IPTG to 0.1 mM at $OD_{550}=1$ or 2, and shake well at 30° C. From OD=2 up to 8 or 10, every half hour or so do the 1. Read the pH with pH sticks 5–10. Adjust to pH 8.5 with 5M NaOH and swirling (2 to 5 ml per liter) whenever the pH falls below 8.
2. Read and record the $OD_{550}$, usually as a 1/10 or 1/50 dilution.
3. This addition of glucose is optional and not necessarily of any value (evaluation of this question is incomplete at this time.) Read the glucose level with glucose sticks, and add an additional 0.5% (10 ml of 50%) if the level falls below 0.2%.

If it is late, the cells can shake at 30° C. all night after the last pH adjustment. Alternatively, set them in the cold room if they have not grown much in a few hours.

Concentrate the cells e.g. by centrifugation in a GS3 rotor for 8 minutes at 8 krpm. Pour off the supernatant and add culture to spin more down onto the same pellets.

Lysis:

Resuspend the cells milliliters of TMN buffer equal to twice the packed cell weight in grams: (50 mM Tris-HCl pH 8.55, 10 mM $MgCl_2$, 16 mM $(NH_4)_2SO_4$).

To each 300 ml of cell suspension add 60 mg lysozyme and incubate the cells at 5°–10° C. with occasional swirling for 15 minutes. Then add NP40 or Triton X100 to 0.1%, and Tween 20 to 0.1%, by adding 1/100 volume of a solution of 10% in each. Then heat the cell suspension rapidly to 80° C. by swirling it in a boiling water bath, then maintain the cells (fast becoming an extract) at 80–81° C. for 20 minutes. Use a clean thermometer in the cells to measure temperature. Be sure the flask and bath are covered, so that even the lip of the flask gets the full heat treatment. After this treatment, which is expected to have inactivated all but a handful of enzymes, cool the extract to 37° C. or lower in an ice bath and add 2 ml of protease inhibitor (100 mM PMSF in isopropanol). From this point forward, try not to contact the preparation with any flask, stir bar, or other object or solution that has not been autoclaved. (Detergents and BME are not autoclavable. The PEI and ammonium sulfate are also not autoclaved.) The purpose of the autoclaving is not only to avoid microbial contamination, but also to avoid contamination with DNA or nucleases.

Distribute into centrifuge bottles and centrifuge at 2° C. (for instance, 30 minutes at 15 krpm in a Sorval SS-34 rotor or 14 h at 4 krpm in a GS3 rotor). The supernatant is designated fraction I, and can be assayed for DNA polymerase activity.

High-salt PEI precipitation

After rendering fraction I 0.25M in NaCl (add 14.6 g per liter), add five percent Polymin-P (PEI, polyethylene-imine, Sigma) dropwise with stirring on ice to precipitate nucleic acids. To determine that adequate Polymin-P has been added, and to avoid addition of more than the minimum amount necessary, test ½ ml of centrifuged extract by adding a drop of Polymin-P, and only if more precipitate forms, add more Polymin-P to the bulk extract, mix and retest. Put the test aliquots of extract back into the bulk without contaminating it.

To confirm that enough PEI has been added, centrifuge 3 ml and aliquot the supernatant into ½ ml aliquots. Add 0, 2, 4, 6 or 10 ul of 5% PEI. Shake, let sit on ice, and centrifuge in the cold. Load 15 ul of these aliquot supernatants onto an agarose gel containing ethidium bromide and electrophorese until the blue dye has travelled 2 cm. Inspect the gel on a UV light box for detectable DNA or RNA in the supernatant. For the bulk extract, use about 1/100 volume (i.e. 2-3 ml for a 300 ml extract) excess 5% PEI over the minimum necessary to remove all DNA by the agarose gel test.

Stir in the cold for at least 15 minutes. Centrifugation of the extract then removes most of the nucleic acids. Keep the supernatant, avoiding any trace of the pellet. Ammonium sulfate precipitation (optional).

This step may be more trouble than it's worth: Although it leads to the removal of some of the PEI so that less of the expensive Bio-Rex 70 is needed in the next step, the A.S. precipitate is not well-behaved (much valuable precipitate actually floats and must be collected by filtration), and a large dilution is necessary to reduce the salt concentration to 22 mM A.S. afterward.

Add mercaptoethanol to 10 mM, and ammonium sulfate to 45% saturation (0.9 volumes of 4M, or 277 g/l). Stir one hour in the cold. Centrifuge, and save all precipitate, whether it floats or sinks.

Different detergent: After the ammonium sulfate precipitation, detergent Thesit (Boehringer-Mannheim) must be present at 0.1% to 0.5% (usually 0.1%) at all times and in all buffers and solutions to which the enzyme is exposed and stored.

Bio-Rex 70 Flow-Through (room temp., but catch flow-through in container on ice).

Chromatography with Bio-Rex 70 (used by Joyce & Grindley) (Joyce, C. M. & Grindley, N. D. E. (1983) Construction of a plasmid that overproduces the large proteolytic fragment (Klenow fragment) of DNA polymerase I of *E. coli*, Proc. Natl. Acad. Sci. U.S.A. 80, 1830-1834)is unsuccessful (no binding), but unavoidable, since without it, the next column (heparin agarose) will not work efficiently. We believe that the important function of the Bio-Rex 70 step is to remove all excess PEI, although it is possible that some protein is removed as well. CM-cellulose does not substitute for Bio-Rex 70.

Resuspend the A.S. precipitate in KTA buffer+-detergents+no salt and dilute it to 22 mM ammonium sulfate. (Check conductivity of 1/40 dilution compared to similar dilution of genuine 22 mM A.S. in KTA.) Pass it through equilibrated Bio-Rex 70 (10 ml per 100 g. cells). The polymerase activity flows through. Rinse the column with 2 column volumes of 22 mM A.S./KTA.

Heparin Agarose Chromatography (room temperature, but put fractions on ice as they come off.)

Load the Bio-Rex flow-through slowly onto heparin agarose (Sigma; 10 ml per 100 grams of cells [this could be too little heparin agarose].) Wash with several column volumes of KTA+22 mM A.S., then three column volumes of KTA+63% glycerol+22 mM A.S., then elute the pure enzyme with KTA+63% glycerol+222 mM A.S.+0.5% Thesit (this is more Thesit for the final eluate.)

Pool the peak of polymerase activity or OD$_{280}$/(starts about at ⅔ of one column volume after 222 mM starts, and is about 2 column volumes wide). Store pool at −20° C.

The storage, buffer is a hybrid of, and a slight variation of, AmpliTaq storage buffer as recommended by Perkin-Elmer Cetus and Taq storage buffer used by Boehringer-Mannheim: 50% glycerol (v/v; 63% w/v), 222 mM ammonium sulfate (diluted to about 50 mM for bench-strength samples), 20 mM Tris-HCl pH 8.55, 0.1 mM EDTA, 10 mM mercaptoethanol, 0.5% Thesit).

The Thesit causes some thickening and cloudiness below −10° C. This seems to cause no harm, but we suggest you warm the enzyme to 0° C. on ice before aliquoting for use. Thesit Replaces the combination of 0.5% Triton-X100, 0.5% Tween 20, which you may want to consider as an alternative.

We have had sporadic reports that freezing can inactivate the enzyme. Exercise caution in this regard. This question is under current investigation.

Our final yield of enzyme from 7 liters (100 g cells) was once 28 ml at a concentration of 120,000 units per ml (4×bench-strength).

¼ ul of bench-strength enzyme will support the PCR of a 2 kb span of DNA in a 100 ul reaction. Template is 5-10 ng of plasmid DNA. Each cycle consists of 1 min 98° C., 1 min 65° C., 6 min 72° C. Cycle number is 16-20. Less enzyme is needed for smaller-sized products (⅛ ul for 500 bp) and more enzyme is needed for larger products (1 ul for 5 kb).

| KTA Buffer | per liter |
|---|---|
| 20 mM Tris 8.55 | 10 ml of 2 M |
| 10 mM BME | 0.7 ml neat |
| 10% w/v Glycerol | 100 g. |
| 0.1 mM EDTA | 0.2 ml of .5 M |
| 0.1% w/v Thesit | 10 ml of 10% |

Rough Incorporation Assay

1×PC2 Buffer (20 mM Tris-HCl pH 8.55, 2.5 mM MgCl$_2$, 16 mM (NH$_4$)$_2$SO$_4$, 100 ug/ml BSA)
200-250 ug/ml activated salmon sperm DNA 40 uM each dNTP+10-50 uCi α-$^{32}$P-dATP per ml To 25 ul assay mix on ice add 0.2 ul of enzyme fraction, undiluted, or diluted in 8 ul of 1×PC2 buffer (or a 1/5 or 1/25 dilution thereof.) Prepare standard Klentaq or Amplitaq, zero enzyme and total input samples, also. Incubate 10 min. at 72° C., then chill. Spot 5 or 8 ul onto filter paper and wash twice for 5-10 min. with 5% TCA, 1% PP$_i$. If pieces of paper were used, count each using Cerenkov radiation or hand monitor. If a single piece of 3 MM paper was used, autoradiograph for 60′.
PCR Assay to give 2 kb product, Make up 1 ml of PCR reaction containing 50 ng of plasmid pLc, 200 pmoles each of primers Lc5 and Lc3, PC2 buffer and 200 uM dNTPs, but no enzyme.

Distribute 100 ul into tube one, and 50 ul into the rest of 8-10 tubes. Add 1 ul of final pool of KlenTaq to tube one and mix. Then remove 50 ul to tube two and mix that, and so on down the series, which will then contain decreasing amounts of enzyme, in two-fold steps. Cover each 50 ul reaction with a drop of mineral off, spin, and PCR 16 cycles at 2′ 95° C., 2′ 65° C., 5′ 72° C.
Final Bench-Strength KlenTaq-278 Enzyme Using 63% glycerol/KTA (0.5% Thesit) buffer with no salt and/or with 50 mM ammonium sulfate, dilute the pool conservatively so that ¼ ul should easily catalyze the amplification the 2 kb span by PCR. Do not

EXAMPLE 4

DNA Amplification

As reported in FIG. 3, a PCR amplification assay to produce 2 kb of DNA product was conducted using *Thermus aquaticus* DNA polymerase (AmpliTaq) (prior art DNA polymerase) and Klentaq-278. To test polymerase thermostability at elevated temperatures, the DNA denaturation step of the PCR amplification reactions were conducted for 2 min. at 97° C., 98° C. and 99° C., respectively, using graduated concentrations of DNA polymerase.

The amplification procedures used followed approximately the protocol for amplifying nucleic acid sequences outlined by Saiki et al., Science 239:487, 1988. A 1 ml reaction mixture was prepared containing 100 ng of plasmid pLC, 200 pmoles each of primers Lc5 and Lc3, reaction buffer (20 mM Tris-HCl pH 8.55, 16 mM ammonium sulfate, 2.5 mM $MgCl_2$ and 150 ug/ml BSA), 200 uM dNTPs, but no enzyme. 100 ul of the reaction mixture was placed into tubes. Aliquots of AmpliTaq and Klentaq-278 were then added and 20 cycles of PCR were undertaken.

FIG. 3 shows the results of the experiment to compare the practical thermostability limits. The only change between the 3 panels shown is the temperature of the 2 min. denaturation step: 97° C., 98° C., or 99° C. A range of enzyme concentrations was used in order to be able to detect small effects on the effective PCR catalysis activity. The template was 10 ng of pLc (a clone of an R color control cDNA from maize. PNAS 86:7092, Science 247:449). The primers were Lc5 37met No. 685 (GTG ATG GAT CCT TCA GCT TCC CGA GTT CAG CAG GCG G)(SEQ ID NO:11) and Lc3 37mer No. 686 (GGT CTC GAG CGA AGC TTC CCT ATA GCT TTG CGA AGA G)(SEQ ID NO:12). Other details of the reactions are given in the assay section of Example 3.

It can be seen in this experiment that 98° C. was not detectably detrimental to KlenTaq-278, yet AT was nearly completely inactivated by this temperature.

In the experiment shown in FIG. 4, each of four enzymes (AT, KlenTaq-278, ST, and KlenTaq-291) was tested for thermostability at 98° C. Each was tested in pairs of two concentrations differing by a factor of 2. The volumes of actual enzyme preparation are indicated above each lane in ul. The amount used was adjusted from previous titrations (conducted as described for the 2 kb PCR assay in Example 3 and the legend to FIG. 3) so that a 2-fold drop-off in activity would be detectable. Note the large amount of ST necessary to function at the 95° C. control PCR. A previous attempt at this experiment (data not shown) used only ¼ these volumes of ST (which would have been equivalent standard DNA polymerase incorporation units compared to KT-291 and KT-278), and no product was obtained.

EXAMPLE 5

Single Colony PCR

The analysis of single *E. coli* colonies by PCR is a convenient screen for the presence and/or orientation of desired DNA fragments during a cloning or recloning procedure. In the prior art, the bacteria may not be simply added to a complete PCR reaction, since they evidently do not lyse efficiently enough to release the plasmid DNA that is to be the template for the PCR. Instead, and cumbersomely, since it requires a complete extra set of labelled test tubes, bacteria must first be suspended in water, not buffer, in the optional but recommended (Riggs et al.) presence of chelating resin, and heated to 100° C. for several (such as 10) minutes. Then 1–10 ul of the heated bacterial suspension is added to an otherwise complete PCR reaction, which is then cycled and analyzed normally.

The improvement here is that, since Klentaq-278 can withstand 98°–99° C. during the denaturation step of each PCR cycle, the bacteria can be added directly and conveniently to a complete (including Klentaq-278 enzyme) PCR reaction and then the PCR cycling can begin without further pretreatment. The only difference from a normal PCR cycling is that the full 98° C. (2 min.) or 99° C. (1 min.) temperature is used during each denaturation step (or at least the first 5–10 steps) of the PCR. The experiment in FIG. 5 used 2 min. at 98° C. for all 25 cycles, and demonstrates that this method gives rise to a more intense and reliably distinguished product band even than the prior art method which utilizes a 10' 100° C. separate treatment. This improvement is not possible with AT enzyme, since AT enzyme is inactivated at 98° C. (as shown in FIGS. 3 and 4).

FIG. 5 is a photograph of an agarose gel of a demonstration of the advantage of a 98° C. denaturation step in colony PCR, compared to the standard 95° C. temperature. Lanes 1 and 3 employed the prior art pre-treatment of the bacteria in distilled water at 100° C. for 10 minutes before addition to the PCR reaction. Lanes 2 and 4 conveniently dispensed with this step and the same amount of bacterial suspension (about 2 to $4 \times 10^6$ cells, but the identical volume of the same bacterial suspension) was simply introduced into the complete PCR reaction (including buffer, triphosphates, primers and enzyme KlenTaq-278.) Lanes 1 and 2 employed the standard 95° C., and lanes 3 and 4 employed the newly possible 98° C. denaturation/cell-disruption temperature. The cycle conditions were 2 min. at 98° C. or 95° C., 2 min. at 65° C., and 5' at 72° C., for 25 cycles. The primers used were KT2 (37mer GAG CCA TGG CCA ACC TGT GGG GGA GGC TTG AGG GGG A) (SEQ ID NO:13) and KlenTaq32 (SEQ ID NO:3)(see FIG. 1). The bacterial cells were X7029 containing plasmid pWB319, a broad-host range plasmid containing the coding region of the gene for KlenTaq-278.

Lane 4 is the most convenient and the most effective method, and it takes advantage of the new stability of KlenTaq-278.

EXAMPLE 6

Efficient and Accurate PCR Amplication of Long DNA Targets

Surprisingly, products in the range 6.6 to 8.4 kb can be efficiently amplified by a formulation of thermostable DNA polymerases consisting of a majority component comprised of at least one thermostable DNA polymerase lacking 3'-exonuclease activity and a minority component comprised of at least one thermostable DNA polymerase exhibiting 3'-exonuclease activity. The prior art technology only allowed relatively inefficient and sporadic amplification of fragments in this size range, resulting in only relatively faint product bands or no detectable product at all. In light of the current discovery, we believe we understand the reason for the inefficiency of the prior art. As speculated in Barnes (1992; supra), *Thermus aquaticus* DNA polymerase and its variants are slow to extend a mismatched base pain (which they cannot remove since they lack any 3'-exonuclease. A couple of companies (New England Biolabs and Stratagene) halve introduced thermostable enzymes which exhibit a 3'-(editing) exonuclease which should, one would think, allow the removal of mismatched bases to result in both efficient extension and more accurately copied products. In practice, these two enzymes (Vent and Pfu DNA polymerase) are unreliable and much less efficient than expected. One possible explanation for the unreliability of these enzymes for PCR is that the 3'-exonuclease often apparently attacks and partially degrades the primers so that little or no PCR is possible. This primer attack problem is worse for some primers than others. It has been reported (Anonymous, The NEB Transcript, New England Biolabs, (March, 1991) p. 4.) that the Vent DNA polymerase leaves the 5' 15 nt intact, so that if the annealling conditions allow that 15 nt to prime, PCR could presumably proceed. This would of course only allow annealling at lower, non-selective temperatures, and the 5' 15 nt of the primers must be exactly homologous to the template.

I have discovered that the expected beneficial effects of a 3'-exonuclease can be obtained with an unexpectedly minute presence of an Archaebacterial DNA polymerase, whilst efficient extension is being catalyzed by a large amount of (3'-exonuclease-free) KlenTaq-278 or AT. The combination, even for KlenTaq-278/Pfu units ratios as high as 2000, exhibited greatly increased efficiency of amplification. When Pfu DNA polymerase was used, the optimal ratio appeared to be in the range 80 to 1000 parts KlenTaq-278 per part (unit) Pfu (my current standard is 640), depending somewhat on primer-template combination. Since the theory is that the exonuclease is removing mismatches to eliminate pausing at the mismatches, the resulting DNA should exhibit, and is expected to exhibit, fewer base pair changes, which is a valuable decrease in the mutagenicity of PCR without sacrificing flexibility, specificity, and efficiency.

Preferred embodiment of the above formulation (designated KlenTaq-LA): Starting with the purified enzymes in storage buffer, mix 1 ul of Pfu DNA polymerase at 2.5 u./ul with 64 ul of KlenTaq-278 at 25 u./ul. Store at −20° C.

Larger amounts of Pfu are detrimental to some PCR amplifications, perform equally for some, and are beneficial for some. For testing of the optimum level of Pfu, several reactions complete with KlenTaq-278 are aliquoted in the amount left to right of 75 ul, 25 ul, 25 ul, and as many additional 25 ul aliquots as desired. Then ⅜ ul of Pfu (equivalent to 0.5 ul per 100 ul—this is about the most that one would ever want) is added to the leftmost, 75 ul reaction and mixed. Serial, two-fold dilutions are then made as 25 ul+25 ul left to right along the row of tubes, adding no Pfu to the last one, as a control of KlenTaq-278 alone. A reaction of ½ or 1 ul (per 100 ul) of Pfu alone should also be run.

Reaction buffer is PC2 as above, supplemented with 200 uM of each dNTP and 800 uM of $MgCl_2$ (total $Mg^{++}$ 3.3 mM), and per 100 ul of reaction volume, 20 pmoles of each primer MBL (SEQ ID NO:7) and MBR (SEQ ID NO:8), and 30 ng of λplac5 intact phage. Per 100 ul of reaction volume, 1 or ½ ul of KTLA are effective levels of enzyme. Suitable PCR cycling conditions are two-temperature: 20 seconds at 94° C., 11 minutes at 70° C., for 20 cycles. Alternate cycling conditions include two-temperature PCR with 1 minute at 98° C. and 10 minutes at 65° C. 10 to 16 ul are loaded onto an agarose gel for product analysis by staining with ethidium bromide. See FIG. 6 for other details and variations.

The template was) λplac5, which carries a portion of the lac operon region of the *E. coli* genome. Thirty ng of phage DNA were included in each 100 ul of reaction volume, introduced as intact phage particles. The primers are homologous to wild-type lambda DNA and amplify λ DNA, not the lac DNA. Primer MBL No. 8757 (5' nucleotide matches base pair 27914 of λ DNA) is GCT TAT CTG CTT CTC ATA GAG TCT TGC (SEQ ID NO:7). Primer MBR No. 8835 (5' nucleotide matches bp 34570 of λ DNA) is ATA ACG ATC ATA TAC ATG GTT CTC TCC (SEQ ID NO:8). The size of the amplified product is therefore predicted to be 6657 bp.

As shown in FIG. 6A and 6B, each DNA polymerase enzyme (KlenTaq-278 or Pfu) alone gives rise to a faint product band (except for some reactions, when Pfu alone does not work at all), but the combinations all give rise to product bands that are 20 to 50 times more intense than either enzyme can catalyze on its own.

FIG. 6C, second lane from the right, shows the surprising result of adding as little as 1/64 ul of Pfu to 1 ul of KlenTaq-278 (a units ratio of 1/640). Not shown are data that as little as 1/200 ul (1/2000 in units) of Pfu contributed a noticeable improvement to the efficiency of this test amplification. Vent DNA polymerase required 10-fold higher amounts (yet stiff minority amounts) for similar functionality.

An additional, beneficial, and unexpected attribute to the PCR reactions catalyzed by KlenTaq-LA was a phenomenal, never previously observed intensity and sharpness to the PCR product bands. In part, this increased yield is manifested by a dark area in the middle of the bands as photographed. This darker area in the ethidium flourescence is believed to be due to UV absorbance by the outside portions of the band, reducing the potential UV-activated flourescence. The system apparently allowed a much greater yield of product then did the prior art, which tended to create a broad smear of product, and increasing amounts of side product, when amplification was allowed to proceed to this extent.

Amplification of 8.4 kb, 12.5 kb, 15 kb, and 18 kb was demonstrated by the experiment depicted in FIG. 7. This experiment extended the demonstrated performance of the currently preferred embodiment of the invention, 1/640 KlenTaq-LA, even further. The amplification was highly successful for the size range 8.4 to 15 kb,, detectably successful for 18 kb, but not successful for an attempted 19.7 kb.

Eight different PCR reactions were run in this experiment, differing from each other in the template or amount of template or in the primer pair employed, as shown in the legend on FIG. 7. Each reaction was divided 3 ways and cycled differently in parts A, B, and C. Between parts A and B, this experiment compared 20 cycles to 30 cycles at 94° denaturation phase. In parts B and C, this experiment compared 94° to 93° for 30 cycles. This experiment utilized 1.3 ul of Klentaq-LA (at a Klentaq-278/Pfu ratio of 640) per 100 ul of reaction. This may have been a little too much enzyme, since high enzyme has been associated in previous experiments with the catastrophic synthesis of product which cannot enter the gel, as occurred here for the reaction products in channels 2B and 6C. At the current stage of development of long PCR using the invention, this poor outcome occurs about 10% of the time.

Comparing conditions B and C, it is apparent that somewhat lower denaturation temperature is desirable. This is consistent with similar experiments comparing time at 94° C., in which yield of long PCR products was found to be decreased as the denaturation time increased in the order 2, 20, 60, and 180 seconds at 94° C. for the denaturation step of each cycle. These data indicated that there was at least one weak link, i.e. least thermostable component, in the reactions which is subject to inactivation at 94°. Since 94° is below the temperature known to damage the DNA polymerase activity and the DNA, it is believed that the critically thermolabile element is the 3'-exonuclease activity. An obvious improvement and extension to the preferred embodiment of the invention would accordingly be the use, as the minority component to replace Pfu DNA polymerase, of a more thermostable 3'-exonuclease of a DNA polymerase such as, but not limited to, that from the Archaebacterium strain ES4, which can grow at temperatures up to 114° C. [Pledger, R. J. and Baross, J. A., J. Gen. Microbiol. 137 (1991)], which maximum growth temperature exceeds that of the source of the Pfu DNA polymerase (103° C.; Blumentals, I. I. et al. (1990) Annals of the N.Y. Acad. Sci. 589:301–314.)

In the experiment in FIG. 7 the final intensity of the 15 kb band matched in only 20 cycles the yield obtained by Kainze et al.supra in 30 cycles for a band of similar size and from similar λDNA template amounts. This was a measure of the improved efficiency provided by the invention, and the further result was that the yield catalyzed by the invention in 30 cycles greatly exceeded the yield reported by these authors for 30 cycles. Accurate quantitation has not yet been carried out to measure the efficiency of the two methods, but inspection of FIG. 7 compared to the figure published by Kainze et al. shows a yield for the 15 kb fragment that is estimated to be some 100 times higher. This corresponds approximately to a doubled efficiency of PCR extension.

The actual upper size limit of products amplified by the new enzyme formulation under optimum cycling conditions is yet unknown, since the optimum cycling conditions have not yet been determined.

In view of the above, it will be seen that the several objects of the invention are achieved and other advantageous results attained. As various changes could be made in the above methods and products without departing from the scope of the invention, it is intended that all matter contained in the above description shall be interpreted as illustrative and not in a limiting sense.

What is claimed is:

1. A DNA polymerase comprising substantially the same amino acid sequence as that of *Thermus aquaticus* DNA polymerase, excluding the N-terminal 280 amino acid residues of *Thermus aquaticus* DNA polymerase.

2. A DNA polymerase as set forth in claim 1, consisting of the amino acid sequence of SEQ ID NO:6.

3. A DNA polymerase as set forth in claim 1 that is encoded by plasmid pWB254b.

4. A DNA polymerase as set forth in claim 1 wherein the DNA polymerase has been purified to be substantially free of other proteins.

5. A DNA polymerase comprising substantially the same amino acid sequence as that of *Thermus flavus* DNA polymerase, excluding the N-terminal 279 amino acid residues of *Thermus flavus* DNA polymerase.

6. A formulation of thermostable DNA polymerases comprising at least one thermostable DNA polymerase lacking 3'-exonuclease activity and at least one thermostable DNA polymerase exhibiting 3'-exonuclease activity, wherein the DNA polymerases are present in a ratio of from about 4 units to about 2000 units of the DNA polymerase lacking 3'-exonuclease activity to 1 unit of the DNA polymerase exhibiting 3'-exonuclease activity.

7. A formulation of thermostable DNA polymerases as set forth in claim 6 wherein the at least one thermostable DNA polymerase lacking 3'-exonuclease activity is the DNA polymerase set forth in claim 1.

8. A formulation of thermostable DNA polymerases as set forth in claim 6 wherein the at least one thermostable DNA polymerase exhibiting 3'-exonuclease activity is selected from the group consisting of Pfu polymerase from *Pyroccus furiosus*, the Vent DNA polymerase from *Thermococcus litoralis*, a variant of the Pfu DNA polymerase wherein the DNA polymerase activity of said Pfu DNA polymerase has been diminished or inactivated, or a variant of the Vent DNA polymerase wherein the DNA polymerase activity of said Vent DNA polymerase has been diminished or inactivated.

9. A formulation of thermostable DNA polymerases as set forth in claim 7 wherein the DNA polymerases are present in a ratio of from about 10 units to about 2000 units of the DNA polymerase lacking 3'-exonuclease activity to 1 unit of the DNA polymerase exhibiting 3'-exonuclease activity.

10. A formulation of thermostable DNA polymerases as set forth in claim 9 wherein the DNA polymerases are present in a ratio of about 640 units of the DNA polymerase lacking 3'-exonuclease activity to 1 unit of the DNA polymerase exhibiting 3'-exonuclease activity.

11. A formulation of DNA polymerases as set forth in claim 6 wherein the DNA polymerases are present in a ratio of from about 10 units to about 2000 units of the DNA polymerase lacking 3'-exonuclease activity to 1 unit of the DNA polymerase exhibiting 3'-exonuclease activity.

12. A formulation of DNA polymerases as set forth in claim 6 wherein the DNA polymerases are present in a ratio of from about 80 units to about 1000 units of the DNA polymerase lacking 3'-exonuclease activity to 1 unit of the DNA polymerase exhibiting 3'-exonuclease activity.

13. A formulation of DNA polymerases as set forth in claim 6 wherein the DNA polymerases are present in a ratio of from about 640 units of the DNA polymerase lacking 3'-exonuclease activity to 1 unit of the DNA polymerase exhibiting 3'-exonuclease activity.

14. A formulation of thermostable DNA polymerases as set forth in claim 6 wherein the at least one thermostable DNA polymerase lacking 3'-exonuclease activity is the DNA polymerase set forth in claim 5.

15. A formulation of thermostable DNA polymerases as set forth in claim 14 wherein the DNA polymerases are present in a ratio of from about 10 units to about 2000 units of the DNA polymerase lacking 3'-exonuclease activity to 1 unit of the DNA polymerase exhibiting 3'-exonuclease activity.

16. A formulation of thermostable DNA polymerases as set forth in claim 15 wherein the DNA polymerases are present in a ratio of about 640 units of the DNA polymerase lacking 3'-exonuclease activity to 1 unit of the DNA polymerase exhibiting 3'-exonuclease activity.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Thermus aquaticus
        ( B ) STRAIN: YT1

( v i i ) IMMEDIATE SOURCE:
        ( A ) LIBRARY: synthetic
        ( B ) CLONE: KT1

( i x ) FEATURE:
        ( A ) NAME/KEY: CDS
        ( B ) LOCATION: 6..35

( x i ) SEQUENCE DESCRIPTION: SEQ ID NO:1:

```
GAGCC ATG GGC CTC CTC CAC GAG TTC GGC CTT CTG G                    36
      Met Gly Leu Leu His Glu Phe Gly Leu Leu
       1               5                  10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear (i i) MOLECULE TYPE: protein (x i) SEQUENCE DESCRIPTION: SEQ ID NO:2:

Met Gly Leu Leu His Glu Phe Gly Leu Leu
1               5                   10

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (v) FRAGMENT TYPE: C-terminal (v i) ORIGINAL SOURCE:
        (A) ORGANISM: Thermus aquaticus
        (B) STRAIN: YT1
        (C) INDIVIDUAL ISOLATE: Klentaq32

(v i i) IMMEDIATE SOURCE:
        (A) LIBRARY: synthetic (i x) FEATURE:
        (A) NAME/KEY: CDS
        (B) LOCATION: complement (8..34)

(x i) SEQUENCE DESCRIPTION: SEQ ID NO:3:

GCGAAGCTTA CTACTCCTTG GCGGAGAGCC AGTC    34

(2) INFORMATION FOR SEQ ID NO:4:

(i) SEQUENCE CHARACTERISTICS:
        (A) LENGTH: 7 amino acids
        (B) TYPE: amino acid
        (D) TOPOLOGY: linear (i i) MOLECULE TYPE: protein (x i) SEQUENCE DESCRIPTION: SEQ ID NO:4:

Asp Trp Leu Ser Ala Lys Glu
1               5

(2) INFORMATION FOR SEQ ID NO:5:

(i) SEQUENCE CHARACTERISTICS:
        (A) LENGTH: 6714 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: NO (i v) ANTI-SENSE: NO (v i) ORIGINAL SOURCE:
        (A) ORGANISM: Expression vector (v i i) IMMEDIATE SOURCE:
        (B) CLONE: pWB254b (i x) FEATURE:
        (A) NAME/KEY: CDS
        (B) LOCATION: 1..1665

(x i) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GGC | CTC | CTC | CAC | GAG | TTC | GGC | CTT | CTG | GAA | AGC | CCC | AAG | GCC | CTG | 48 |
| Met | Gly | Leu | Leu | His | Glu | Phe | Gly | Leu | Leu | Glu | Ser | Pro | Lys | Ala | Leu | |
| 1 | | | | 5 | | | | | 10 | | | | | 15 | | |
| GAG | GAG | GCC | CCC | TGG | CCC | CCG | CCG | GAA | GGG | GCC | TTC | GTG | GGC | TTT | GTG | 96 |
| Glu | Glu | Ala | Pro | Trp | Pro | Pro | Pro | Glu | Gly | Ala | Phe | Val | Gly | Phe | Val | |
| | | | 20 | | | | | 25 | | | | | 30 | | | |
| CTT | TCC | CGC | AAG | GAG | CCC | ATG | TGG | GCC | GAT | CTT | CTG | GCC | CTG | GCC | GCC | 144 |
| Leu | Ser | Arg | Lys | Glu | Pro | Met | Trp | Ala | Asp | Leu | Leu | Ala | Leu | Ala | Ala | |
| | | 35 | | | | 40 | | | | | 45 | | | | | |
| GCC | AGG | GGG | GGC | CGG | GTC | CAC | CGG | GCC | CCC | GAG | CCT | TAT | AAA | GCC | CTC | 192 |
| Ala | Arg | Gly | Gly | Arg | Val | His | Arg | Ala | Pro | Glu | Pro | Tyr | Lys | Ala | Leu | |
| | 50 | | | | | 55 | | | | | 60 | | | | | |
| AGG | GAC | CTG | AAG | GAG | GCG | CGG | GGG | CTT | CTC | GCC | AAA | GAC | CTG | AGC | GTT | 240 |
| Arg | Asp | Leu | Lys | Glu | Ala | Arg | Gly | Leu | Leu | Ala | Lys | Asp | Leu | Ser | Val | |
| 65 | | | | 70 | | | | | 75 | | | | | 80 | | |
| CTG | GCC | CTG | AGG | GAA | GGC | CTT | GGC | CTC | CCG | CCC | GGC | GAC | GAC | CCC | ATG | 288 |
| Leu | Ala | Leu | Arg | Glu | Gly | Leu | Gly | Leu | Pro | Pro | Gly | Asp | Asp | Pro | Met | |
| | | | 85 | | | | | 90 | | | | | 95 | | | |
| CTC | CTC | GCC | TAC | CTC | CTG | GAC | CCT | TCC | AAC | ACC | ACC | CCC | GAG | GGG | GTG | 336 |
| Leu | Leu | Ala | Tyr | Leu | Leu | Asp | Pro | Ser | Asn | Thr | Thr | Pro | Glu | Gly | Val | |
| | | | 100 | | | | | 105 | | | | | 110 | | | |
| GCC | CGG | CGC | TAC | GGC | GGG | GAG | TGG | ACG | GAG | GAG | GCG | GGG | GAG | CGG | GCC | 384 |
| Ala | Arg | Arg | Tyr | Gly | Gly | Glu | Trp | Thr | Glu | Glu | Ala | Gly | Glu | Arg | Ala | |
| | | 115 | | | | | 120 | | | | | 125 | | | | |
| GCC | CTT | TCC | GAG | AGG | CTC | TTC | GCC | AAC | CTG | TGG | GGG | AGG | CTT | GAG | GGG | 432 |
| Ala | Leu | Ser | Glu | Arg | Leu | Phe | Ala | Asn | Leu | Trp | Gly | Arg | Leu | Glu | Gly | |
| | 130 | | | | | 135 | | | | | 140 | | | | | |
| GAG | GAG | AGG | CTC | CTT | TGG | CTT | TAC | CGG | GAG | GTG | GAG | AGG | CCC | CTT | TCC | 480 |
| Glu | Glu | Arg | Leu | Leu | Trp | Leu | Tyr | Arg | Glu | Val | Glu | Arg | Pro | Leu | Ser | |
| 145 | | | | | 150 | | | | | 155 | | | | | 160 | |
| GCT | GTC | CTG | GCC | CAC | ATG | GAG | GCC | ACG | GGG | GTG | CGC | CTG | GAC | GTG | GCC | 528 |
| Ala | Val | Leu | Ala | His | Met | Glu | Ala | Thr | Gly | Val | Arg | Leu | Asp | Val | Ala | |
| | | | | 165 | | | | | 170 | | | | | 175 | | |
| TAT | CTC | AGG | GCC | TTG | TCC | CTG | GAG | GTG | GCC | GAG | GAG | ATC | GCC | CGC | CTC | 576 |
| Tyr | Leu | Arg | Ala | Leu | Ser | Leu | Glu | Val | Ala | Glu | Glu | Ile | Ala | Arg | Leu | |
| | | | 180 | | | | | 185 | | | | | 190 | | | |
| GAG | GCC | GAG | GTC | TTC | CGC | CTG | GCC | GGC | CAC | CCC | TTC | AAC | CTC | AAC | TCC | 624 |
| Glu | Ala | Glu | Val | Phe | Arg | Leu | Ala | Gly | His | Pro | Phe | Asn | Leu | Asn | Ser | |
| | | 195 | | | | | 200 | | | | | 205 | | | | |
| CGG | GAC | CAG | CTG | GAA | AGG | GTC | CTC | TTT | GAC | GAG | CTA | GGG | CTT | CCC | GCC | 672 |
| Arg | Asp | Gln | Leu | Glu | Arg | Val | Leu | Phe | Asp | Glu | Leu | Gly | Leu | Pro | Ala | |
| | 210 | | | | | 215 | | | | | 220 | | | | | |
| ATC | GGC | AAG | ACG | GAG | AAG | ACC | GGC | AAG | CGC | TCC | ACC | AGC | GCC | GCC | GTC | 720 |
| Ile | Gly | Lys | Thr | Glu | Lys | Thr | Gly | Lys | Arg | Ser | Thr | Ser | Ala | Ala | Val | |
| 225 | | | | 230 | | | | | 235 | | | | | 240 | | |
| CTG | GAG | GCC | CTC | CGC | GAG | GCC | CAC | CCC | ATC | GTG | GAG | AAG | ATC | CTG | CAG | 768 |
| Leu | Glu | Ala | Leu | Arg | Glu | Ala | His | Pro | Ile | Val | Glu | Lys | Ile | Leu | Gln | |
| | | | | 245 | | | | | 250 | | | | | 255 | | |
| TAC | CGG | GAG | CTC | ACC | AAG | CTG | AAG | AGC | ACC | TAC | ATT | GAC | CCC | TTG | CCG | 816 |
| Tyr | Arg | Glu | Leu | Thr | Lys | Leu | Lys | Ser | Thr | Tyr | Ile | Asp | Pro | Leu | Pro | |
| | | | 260 | | | | | 265 | | | | | 270 | | | |
| GAC | CTC | ATC | CAC | CCC | AGG | ACG | GGC | CGC | CTC | CAC | ACC | CGC | TTC | AAC | CAG | 864 |
| Asp | Leu | Ile | His | Pro | Arg | Thr | Gly | Arg | Leu | His | Thr | Arg | Phe | Asn | Gln | |
| | | 275 | | | | | 280 | | | | | 285 | | | | |
| ACG | GCC | ACG | GCC | ACG | GGC | AGG | CTA | AGT | AGC | TCC | GAT | CCC | AAC | CTC | CAG | 912 |
| Thr | Ala | Thr | Ala | Thr | Gly | Arg | Leu | Ser | Ser | Ser | Asp | Pro | Asn | Leu | Gln | |
| | 290 | | | | | 295 | | | | | 300 | | | | | |
| AAC | ATC | CCC | GTC | CGC | ACC | CCG | CTT | GGG | CAG | AGG | ATC | GCC | CGG | GCC | TTC | 960 |
| Asn | Ile | Pro | Val | Arg | Thr | Pro | Leu | Gly | Gln | Arg | Ile | Arg | Arg | Ala | Phe | |
| 305 | | | | 310 | | | | | 315 | | | | | 320 | | |
| ATC | GCC | GAG | GAG | GGG | TGG | CTA | TTG | GTG | GCC | CTG | GAC | TAT | AGC | CAG | ATA | 1008 |

|     |     |     |     |     |     |     |     |     |     |     |     |     |     |     |      |
|-----|-----|-----|-----|-----|-----|-----|-----|-----|-----|-----|-----|-----|-----|-----|------|
| Ile | Ala | Glu | Glu | Gly | Trp | Leu | Leu | Val | Ala | Leu | Asp | Tyr | Ser | Gln | Ile  |
|     |     |     |     | 325 |     |     |     |     | 330 |     |     |     |     | 335 |      |

| GAG | CTC | AGG | GTG | CTG | GCC | CAC | CTC | TCC | GGC | GAC | GAG | AAC | CTG | ATC | CGG | 1056 |
|-----|-----|-----|-----|-----|-----|-----|-----|-----|-----|-----|-----|-----|-----|-----|-----|------|
| Glu | Leu | Arg | Val | Leu | Ala | His | Leu | Ser | Gly | Asp | Glu | Asn | Leu | Ile | Arg |      |
|     |     |     | 340 |     |     |     |     | 345 |     |     |     |     | 350 |     |     |      |

| GTC | TTC | CAG | GAG | GGG | CGG | GAC | ATC | CAC | ACG | GAG | ACC | GCC | AGC | TGG | ATG | 1104 |
|-----|-----|-----|-----|-----|-----|-----|-----|-----|-----|-----|-----|-----|-----|-----|-----|------|
| Val | Phe | Gln | Glu | Gly | Arg | Asp | Ile | His | Thr | Glu | Thr | Ala | Ser | Trp | Met |      |
|     |     | 355 |     |     |     |     | 360 |     |     |     |     | 365 |     |     |     |      |

| TTC | GGC | GTC | CCC | CGG | GAG | GCC | GTG | GAC | CCC | CTG | ATG | CGC | CGG | GCG | GCC | 1152 |
|-----|-----|-----|-----|-----|-----|-----|-----|-----|-----|-----|-----|-----|-----|-----|-----|------|
| Phe | Gly | Val | Pro | Arg | Glu | Ala | Val | Asp | Pro | Leu | Met | Arg | Arg | Ala | Ala |      |
|     | 370 |     |     |     |     | 375 |     |     |     |     | 380 |     |     |     |     |      |

| AAG | ACC | ATC | AAC | TTC | GGG | GTC | CTC | TAC | GGC | ATG | TCG | GCC | CAC | CGC | CTC | 1200 |
|-----|-----|-----|-----|-----|-----|-----|-----|-----|-----|-----|-----|-----|-----|-----|-----|------|
| Lys | Thr | Ile | Asn | Phe | Gly | Val | Leu | Tyr | Gly | Met | Ser | Ala | His | Arg | Leu |      |
| 385 |     |     |     |     | 390 |     |     |     |     | 395 |     |     |     |     | 400 |      |

| TCC | CAG | GAG | CTA | GCC | ATC | CCT | TAC | GAG | GAG | GCC | CAG | GCC | TTC | ATT | GAG | 1248 |
|-----|-----|-----|-----|-----|-----|-----|-----|-----|-----|-----|-----|-----|-----|-----|-----|------|
| Ser | Gln | Glu | Leu | Ala | Ile | Pro | Tyr | Glu | Glu | Ala | Gln | Ala | Phe | Ile | Glu |      |
|     |     |     |     | 405 |     |     |     |     | 410 |     |     |     |     | 415 |     |      |

| CGC | TAC | TTT | CAG | AGC | TTC | CCC | AAG | GTG | CGG | GCC | TGG | ATT | GAG | AAG | ACC | 1296 |
|-----|-----|-----|-----|-----|-----|-----|-----|-----|-----|-----|-----|-----|-----|-----|-----|------|
| Arg | Tyr | Phe | Gln | Ser | Phe | Pro | Lys | Val | Arg | Ala | Trp | Ile | Glu | Lys | Thr |      |
|     |     |     | 420 |     |     |     |     | 425 |     |     |     |     | 430 |     |     |      |

| CTG | GAG | GAG | GGC | AGG | AGG | CGG | GGG | TAC | GTG | GAG | ACC | CTC | TTC | GGC | CGC | 1344 |
|-----|-----|-----|-----|-----|-----|-----|-----|-----|-----|-----|-----|-----|-----|-----|-----|------|
| Leu | Glu | Glu | Gly | Arg | Arg | Arg | Gly | Tyr | Val | Glu | Thr | Leu | Phe | Gly | Arg |      |
|     |     | 435 |     |     |     |     | 440 |     |     |     |     | 445 |     |     |     |      |

| CGC | CGC | TAC | GTG | CCA | GAC | CTA | GAG | GCC | CGG | GTG | AAG | AGC | GTG | CGG | GAG | 1392 |
|-----|-----|-----|-----|-----|-----|-----|-----|-----|-----|-----|-----|-----|-----|-----|-----|------|
| Arg | Arg | Tyr | Val | Pro | Asp | Leu | Glu | Ala | Arg | Val | Lys | Ser | Val | Arg | Glu |      |
| 450 |     |     |     |     | 455 |     |     |     |     | 460 |     |     |     |     |     |      |

| GCG | GCC | GAG | CGC | ATG | GCC | TTC | AAC | ATG | CCC | GTC | CAG | GGC | ACC | GCC | GCC | 1440 |
|-----|-----|-----|-----|-----|-----|-----|-----|-----|-----|-----|-----|-----|-----|-----|-----|------|
| Ala | Ala | Glu | Arg | Met | Ala | Phe | Asn | Met | Pro | Val | Gln | Gly | Thr | Ala | Ala |      |
| 465 |     |     |     | 470 |     |     |     |     | 475 |     |     |     |     | 480 |     |      |

| GAC | CTC | ATG | AAG | CTG | GCT | ATG | GTG | AAG | CTC | TTC | CCC | AGG | CTG | GAG | GAA | 1488 |
|-----|-----|-----|-----|-----|-----|-----|-----|-----|-----|-----|-----|-----|-----|-----|-----|------|
| Asp | Leu | Met | Lys | Leu | Ala | Met | Val | Lys | Leu | Phe | Pro | Arg | Leu | Glu | Glu |      |
|     |     |     |     | 485 |     |     |     |     | 490 |     |     |     |     | 495 |     |      |

| ATG | GGG | GCC | AGG | ATG | CTC | CTT | CAG | GTC | CAC | GAC | GAG | CTG | GTC | CTC | GAG | 1536 |
|-----|-----|-----|-----|-----|-----|-----|-----|-----|-----|-----|-----|-----|-----|-----|-----|------|
| Met | Gly | Ala | Arg | Met | Leu | Leu | Gln | Val | His | Asp | Glu | Leu | Val | Leu | Glu |      |
|     |     |     | 500 |     |     |     |     | 505 |     |     |     |     | 510 |     |     |      |

| GCC | CCA | AAA | GAG | AGG | GCG | GAG | GCC | GTG | GCC | CGG | CTG | GCC | AAG | GAG | GTC | 1584 |
|-----|-----|-----|-----|-----|-----|-----|-----|-----|-----|-----|-----|-----|-----|-----|-----|------|
| Ala | Pro | Lys | Glu | Arg | Ala | Glu | Ala | Val | Ala | Arg | Leu | Ala | Lys | Glu | Val |      |
|     |     | 515 |     |     |     |     | 520 |     |     |     |     | 525 |     |     |     |      |

| ATG | GAG | GGG | GTG | TAT | CCC | CTG | GCC | GTG | CCC | CTG | GAG | GTG | GAG | GTG | GGG | 1632 |
|-----|-----|-----|-----|-----|-----|-----|-----|-----|-----|-----|-----|-----|-----|-----|-----|------|
| Met | Glu | Gly | Val | Tyr | Pro | Leu | Ala | Val | Pro | Leu | Glu | Val | Glu | Val | Gly |      |
|     | 530 |     |     |     |     | 535 |     |     |     |     | 540 |     |     |     |     |      |

| ATA | GGG | GAG | GAC | TGG | CTC | TCC | GCC | AAG | GAG | TAGTAAGCTT | ATCGATGATA | 1682 |
|-----|-----|-----|-----|-----|-----|-----|-----|-----|-----|------------|------------|------|
| Ile | Gly | Glu | Asp | Trp | Leu | Ser | Ala | Lys | Glu |            |            |      |
| 545 |     |     |     |     | 550 |     |     |     | 555 |            |            |      |

| AGCTGTCAAA | CATGAGAATT | AGCCCGCCTA | ATGAGCGGGC | TTTTTTTAA  | TTCTTGAAGA | 1742 |
|------------|------------|------------|------------|------------|------------|------|
| CGAAAGGGCC | TCGTGATACG | CCTATTTTTA | TAGGTTAATG | TCATGATAAT | AATGGTTTCT | 1802 |
| TAGCGTCAAA | GCAACCATAG | TACGCGCCCT | GTAGCGGCGC | ATTAAGCGCG | CCGGGTGTGG | 1862 |
| TGGTTACGCG | CAGCGTGACC | GCTACACTTG | CCAGCGCCCT | AGCGCCCGCT | CCTTTCGCTT | 1922 |
| TCTTCCCTTC | CTTTCTCGCC | ACGTTCGCCG | GCTTTCCCCG | TCAAGCTCTA | AATCGGGGGC | 1982 |
| TCCCTTTAGG | GTTCCGATTT | AGTGCTTTAC | GGCACCTCGA | CCCCAAAAAA | CTTGATTTGG | 2042 |
| GTGATGGTTC | ACGTAGTGGG | CCATCGCCCT | GATAGACGGT | TTTTCGCCCT | TTGACGTTGG | 2102 |
| AGTCCACGTT | CTTTAATAGT | GGACTCTTGT | TCCAAACTTG | AACAACACTC | AACCCTATCT | 2162 |
| CGGGCTATTC | TTTTGATTTA | TAAGGGATTT | TGCCGATTTC | GGCCTATTGG | TTAAAAATG  | 2222 |
| AGCTGATTTA | ACAAAAATTT | AACGCGAATT | TTAACAAAAT | ATTAACGTTT | ACAATTTCAG | 2282 |
| GTGGCACTTT | TCGGGGAAAT | GTGCGCGGAA | CCCCTATTTG | TTTATTTTTC | TAAATACATT | 2342 |
| CAAATATGTA | TCCGCTCATG | AGACAATAAC | CCTGATAAAT | GCTTCAATAA | TATTGAAAAA | 2402 |

```
GGAAGAGTAT GAGTATTCAA CATTTCCGTG TCGCCCTTAT TCCCTTTTTT GCGGCATTTT      2462
GCCTTCCTGT TTTTGCTCAC CCAGAAACGC TGGTGAAAGT AAAAGATGCT GAAGATCAGT      2522
TGGGTGCACG AGTGGGTTAC ATCGAACTGG ATCTCAACAG CGGTAAGATC CTTGAGAGTT      2582
TTCGCCCCGA AGAACGTTTT CCAATGATGA GCACTTTTAA AGTTCTGCTA TGTGGCGCGG      2642
TATTATCCCG TGTTGACGCC GGGCAAGAGC AACTCGGTCG CCGCATACAC TATTCTCAGA      2702
ATGACTTGGT TGAGTACTCA CCAGTCACAG AAAAGCATCT TACGGATGGC ATGACAGTAA      2762
GAGAATTATG CAGTGCTGCC ATAACCATGA GTGATAACAC TGCGGCCAAC TTACTTCTGA      2822
CAACGATCGG AGGACCGAAG GAGCTAACCG CTTTTTTGCA CAACATGGGG GATCATGTAA      2882
CTCGCCTTGA TCGTTGGGAA CCGGAGCTGA ATGAAGCCAT ACCAAACGAC GAGCGTGACA      2942
CCACGATGCC TGCAGCAATG GCAACAACGT TGCGCAAACT ATTAACTGGC GAACTACTTA      3002
CTCTAGCTTC CCGGCAACAA TTAATAGACT GGATGGAGGC GGATAAAGTT GCAGGACCAC      3062
TTCTGCGCTC GGCCCTTCCG GCTGGCTGGT TTATTGCTGA TAAATCTGGA GCCGGTGAGC      3122
GTGGGTCTCG CGGTATCATT GCAGCACTGG GGCCAGATGG TAAGCCCTCC CGTATCGTAG      3182
TTATCTACAC GACGGGGAGT CAGGCAACTA TGGATGAACG AAATAGACAG ATCGCTGAGA      3242
TAGGTGCCTC ACTGATTAAG CATTGGTAAC TGTCAGACCA AGTTTACTCA TATATACTTT      3302
AGATTGATTT AAAACTTCAT TTTTAATTTA AAAGGATCTA GGTGAAGATC CTTTTTGATA      3362
ATCTCATGAC CAAAATCCCT TAACGTGAGT TTTCGTTCCA CTGAGCGTCA GACCCCGTAG      3422
AAAAGATCAA AGGATCTTCT TGAGATCCTT TTTTTCTGCG CGTAATCTGC TGCTTGCAAA      3482
CAAAAAAACC ACCGCTACCA GCGGTGGTTT GTTTGCCGGA TCAAGAGCTA CCAACTCTTT      3542
TTCCGAAGGT AACTGGCTTC AGCAGAGCGC AGATACCAAA TACTGTCCTT CTAGTGTAGC      3602
CGTAGTTAGG CCACCACTTC AAGAACTCTG TAGCACCGCC TACATACCTC GCTCTGCTAA      3662
TCCTGTTACC AGTGGCTGCT GCCAGTGGCG ATAAGTCGTG TCTTACCGGG TTGGACTCAA      3722
GACGATAGTT ACCGGATAAG GCGCAGCGGT CGGGCTGAAC GGGGGGTTCG TGCACACAGC      3782
CCAGCTTGGA GCGAACGACC TACACCGAAC TGAGATACCT ACAGCGTGAG CTATGAGAAA      3842
GCGCCACGCT TCCCGAAGGG AGAAAGGCGG ACAGGTATCC GGTAAGCGGC AGGGTCGGAA      3902
CAGGAGAGCG CACGAGGGAG CTTCCAGGGG GAAACGCCTG GTATCTTTAT AGTCCTGTCG      3962
GGTTTCGCCA CCTCTGACTT GAGCGTCGAT TTTTGTGATG CTCGTCAGGG GGGCGGAGCC      4022
TATGGAAAAA CGCCAGCAAC GCGGCCTTTT TACGGTTCCT GGCCTTTTGC TGGCCTTTTG      4082
CTCACATGTT CTTTCCTGCG TTATCCCCTG ATTCTGTGGA TAACCGTATT ACCGCCTTTG      4142
AGTGAGCTGA TACCGCTCGC CGCAGCCGAA CGACCGAGCG CAGCGAGTCA GTGAGCGAGG      4202
AAGCGGAAGA GCGCCTGATG CGGTATTTTC TCCTTACGCA TCTGTGCGGT ATTTCACACC      4262
GCATATGGTG CACTCTCAGT ACAATCTGCT CTGATGCCGC ATAGTTAAGC CAGTATACAC      4322
TCCGCTATCG CTACGTGACT GGGTCATGGC TGCGCCCCGA CACCCGCCAA CACCCGCTGA      4382
CGCGCCCTGA CGGGCTTGTC TGCTCCCGGC ATCCGCTTAC AGACAAGCTG TGACCGTCTC      4442
CGGGAGCTGC ATGTGTCAGA GGTTTTCACC GTCATCACCG AAACGCGCGA GGCAGAACGC      4502
CATCAAAAAT AATTCGCGTC TGGCCTTCCT GTAGCCAGCT TTCATCAACA TTAAATGTGA      4562
GCGAGTAACA ACCCGTCGGA TTCTCCGTGG GAACAAACGG CGGATTGACC GTAATGGGAT      4622
AGGTTACGTT GGTGTAGATG GGCGCATCGT AACCGTGCAT CTGCCAGTTT GAGGGGACGA      4682
CGACAGTATC GGCCTCAGGA AGATCGCACT CCAGCCAGCT TTCCGGCACC GCTTCTGGTG      4742
CCGGAAACCA GGCAAAGCGC CATTCGCCAT TCAGGCTGCG CAACTGTTGG GAAGGGCGAT      4802
CGGTGCGGGC CTCTTCGCTA TTACGCCAGC TGGCGAAAGG GGGATGTGCT GCAAGGCGAT      4862
```

-continued

```
TAAGTTGGGT AACGCCAGGG TTTTCCCAGT CACGACGTTG TAAAACGACG GCCAGTGAAT    4922
CCGTAATCAT GGTCATAGCT GTTTCCTGTG TGAAATTGTT ATCCGCTCAC AATTCCACAC    4982
AACATACGAG CCGGAAGCAT AAAGTGTAAA GCCTGGGGTG CCTAATGAGT GAGCTAACTC    5042
ACATTAATTG CGTTGCGCTC ACTGCCCGCT TTCCAGTCGG GAAACCTGTC GTGCCAGCTG    5102
CATTAATGAA TCGGCCAACG CGCGGGGAGA GGCGGTTTGC GTATTGGGCG CCAGGGTGGT    5162
TTTTCTTTTC ACCAGTGAGA CGGGCAACAG CTGATTGCCC TTCACCGCCT GGCCCTGAGA    5222
GAGTTGCAGC AAGCGGTCCA CGCTGGTTTG CCCCAGCAGG CGAAAATCCT GTTTGATGGT    5282
GGTTGACGGC GGGATATAAC ATGAGCTGTC TTCGGTATCG TCGTATCCCA CTACCGAGAT    5342
ATCCGCACCA ACGCGCAGCC CGGACTCGGT AATGGCGCGC ATTGCGCCCA GCGCCATCTG    5402
ATCGTTGGCA ACCAGCATCG CAGTGGGAAC GATGCCCTCA TTCAGCATTT GCATGGTTTG    5462
TTGAAAACCG GACATGGCAC TCCAGTCGCC TTCCCGTTCC GCTATCGGCT GAATTTGATT    5522
GCGAGTGAGA TATTTATGCC AGCCAGCCAG ACGCAGACGC GCCGAGACAG AACTTAATGG    5582
GCCCGCTAAC AGCGCGATTT GCTGGTGACC CAATGCGACC AGATGCTCCA CGCCCAGTCG    5642
CGTACCGTCT TCATGGGAGA AAATAATACT GTTGATGGGT GTCTGGTCAG AGACATCAAG    5702
AAATAACGCC GGAACATTAG TGCAGGCAGC TTCCACAGCA ATGGCATCCT GGTCATCCAG    5762
CGGATAGTTA ATGATCAGCC CACTGACGCG TTGCGCGAGA AGATTGTGCA CCGCCGCTTT    5822
ACAGGCTTCG ACGCCGCTTC GTTCTACCAT CGACACCACC ACGCTGGCAC CCAGTTGATC    5882
GGCGCGAGAT TAATCGCCG CGACAATTTG CGACGGCGCG TGCAGGGCCA GACTGGAGGT    5942
GGCAACGCCA ATCAGCAACG ACTGTTTGCC CGCCAGTTGT TGTGCCACGC GGTTGGGAAT    6002
GTAATTCAGC TCCGCCATCG CCGCTTCCAC TTTTCCCGC GTTTTCGCAG AAACGTGGCT    6062
GGCCTGGTTC ACCACGCGGG AAACGGTCTG ATAAGAGACA CCGGCATACT CTGCGACATC    6122
GTATAACGTT ACTGGTTTCA CATTCACCAC CCTGAATTGA CTCTCTTCCG GGCGCTATCA    6182
TGCCATACCG CGAAAGGTTT TGCGCCATTC GATGGTGTCC CAGTGAATCC GTAATCATGG    6242
TCATAGCTGT TTCCTGTGTG AAATTGTTAT CCGCTCACAA TTCCACACAT TATACGAGCC    6302
GGAAGCATAA AGTGTAAAGC CTGGGGTGCC TAATGAGTGA GCTAACTCAC ATTAATTGCG    6362
TTGCGCTCAC TGCCCGCTTT CCAGTCGGGA AACCTGTCGT GCCAGCTGCA TTAATGAATC    6422
GGAGCTTACT CCCCATCCCC CTGTTGACAA TTAATCATCG GCTCGTATAA TGTGTGGAAT    6482
TGTGAGCGGA TAACAATTTC ACACAGGAAA CAGGATCGAT CCAGCTTACT CCCCATCCCC    6542
CTGTTGACAA TTAATCATCG GCTCGTATAA TGTGTGGAAT TGTGAGCGGA TAACAATTTC    6602
ACACAGGAAA CAGGATCTGG GCCCTTCGAA ATTAATACGA CTCACTATAG GAGACCACA    6662
ACGGTTTCCC TCTAGAAATA ATTTTGTTTA ACTTTAAGAA GGAGATATAT CC          6714
```

( 2 ) INFORMATION FOR SEQ ID NO:6:

( i ) SEQUENCE CHARACTERISTICS:
        ( A ) LENGTH: 554 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gly Leu Leu His Glu Phe Gly Leu Leu Glu Ser Pro Lys Ala Leu
 1               5                  10                  15

Glu Glu Ala Pro Trp Pro Pro Pro Glu Gly Ala Phe Val Gly Phe Val
            20                  25                  30

Leu Ser Arg Lys Glu Pro Met Trp Ala Asp Leu Leu Ala Leu Ala Ala
```

|  |  |  |  |  | 35 |  |  |  |  | 40 |  |  |  |  | 45 |  |  |
|---|---|---|---|---|---|---|---|---|---|---|---|---|---|---|---|---|---|

Ala Arg Gly Gly Arg Val His Arg Ala Pro Glu Pro Tyr Lys Ala Leu
　　　50　　　　　　　　　55　　　　　　　　　60

Arg Asp Leu Lys Glu Ala Arg Gly Leu Leu Ala Lys Asp Leu Ser Val
65　　　　　　　　　70　　　　　　　　　75　　　　　　　　　80

Leu Ala Leu Arg Glu Gly Leu Gly Leu Pro Pro Gly Asp Asp Pro Met
　　　　　　　85　　　　　　　　　90　　　　　　　　　95

Leu Leu Ala Tyr Leu Leu Asp Pro Ser Asn Thr Thr Pro Glu Gly Val
　　　　　100　　　　　　　　105　　　　　　　　　110

Ala Arg Arg Tyr Gly Gly Glu Trp Thr Glu Glu Ala Gly Glu Arg Ala
　　　115　　　　　　　　120　　　　　　　　125

Ala Leu Ser Glu Arg Leu Phe Ala Asn Leu Trp Gly Arg Leu Glu Gly
　　　130　　　　　　　　135　　　　　　　　140

Glu Glu Arg Leu Leu Trp Leu Tyr Arg Glu Val Glu Arg Pro Leu Ser
145　　　　　　　　150　　　　　　　　155　　　　　　　　160

Ala Val Leu Ala His Met Glu Ala Thr Gly Val Arg Leu Asp Val Ala
　　　　　　　165　　　　　　　　170　　　　　　　　175

Tyr Leu Arg Ala Leu Ser Leu Glu Val Ala Glu Glu Ile Ala Arg Leu
　　　　　180　　　　　　　　185　　　　　　　　190

Glu Ala Glu Val Phe Arg Leu Ala Gly His Pro Phe Asn Leu Asn Ser
　　　195　　　　　　　　200　　　　　　　　205

Arg Asp Gln Leu Glu Arg Val Leu Phe Asp Glu Leu Gly Leu Pro Ala
　　　210　　　　　　　　215　　　　　　　　220

Ile Gly Lys Thr Glu Lys Thr Gly Lys Arg Ser Thr Ser Ala Ala Val
225　　　　　　　　230　　　　　　　　235　　　　　　　　240

Leu Glu Ala Leu Arg Glu Ala His Pro Ile Val Glu Lys Ile Leu Gln
　　　　　　　245　　　　　　　　250　　　　　　　　255

Tyr Arg Glu Leu Thr Lys Leu Lys Ser Thr Tyr Ile Asp Pro Leu Pro
　　　　　260　　　　　　　　265　　　　　　　　270

Asp Leu Ile His Pro Arg Thr Gly Arg Leu His Thr Arg Phe Asn Gln
　　　275　　　　　　　　280　　　　　　　　285

Thr Ala Thr Ala Thr Gly Arg Leu Ser Ser Ser Asp Pro Asn Leu Gln
　　　290　　　　　　　　295　　　　　　　　300

Asn Ile Pro Val Arg Thr Pro Leu Gly Gln Arg Ile Arg Arg Ala Phe
305　　　　　　　　310　　　　　　　　315　　　　　　　　320

Ile Ala Glu Glu Gly Trp Leu Leu Val Ala Leu Asp Tyr Ser Gln Ile
　　　　　　　325　　　　　　　　330　　　　　　　　335

Glu Leu Arg Val Leu Ala His Leu Ser Gly Asp Glu Asn Leu Ile Arg
　　　　　340　　　　　　　　345　　　　　　　　350

Val Phe Gln Glu Gly Arg Asp Ile His Thr Glu Thr Ala Ser Trp Met
　　　355　　　　　　　　360　　　　　　　　365

Phe Gly Val Pro Arg Glu Ala Val Asp Pro Leu Met Arg Arg Ala Ala
　　　370　　　　　　　　375　　　　　　　　380

Lys Thr Ile Asn Phe Gly Val Leu Tyr Gly Met Ser Ala His Arg Leu
385　　　　　　　　390　　　　　　　　395　　　　　　　　400

Ser Gln Glu Leu Ala Ile Pro Tyr Glu Glu Ala Gln Ala Phe Ile Glu
　　　　　　　405　　　　　　　　410　　　　　　　　415

Arg Tyr Phe Gln Ser Phe Pro Lys Val Arg Ala Trp Ile Glu Lys Thr
　　　　　420　　　　　　　　425　　　　　　　　430

Leu Glu Glu Gly Arg Arg Arg Gly Tyr Val Glu Thr Leu Phe Gly Arg
　　　435　　　　　　　　440　　　　　　　　445

Arg Arg Tyr Val Pro Asp Leu Glu Ala Arg Val Lys Ser Val Arg Glu
　　　450　　　　　　　　455　　　　　　　　460

Ala Ala Glu Arg Met Ala Phe Asn Met Pro Val Gln Gly Thr Ala Ala
465　　　　　　　　470　　　　　　　　475　　　　　　　　480

| | | | | | | | | | | | | |
|---|---|---|---|---|---|---|---|---|---|---|---|---|
|Asp|Leu|Met|Lys<br>485|Leu|Ala|Met|Val|Lys<br>490|Leu|Phe|Pro|Arg|Leu|Glu<br>495|Glu|

Met Gly Ala Arg Met Leu Leu Gln Val His Asp Glu Leu Val Leu Glu
            500                     505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
    530                 535                 540

Ile Gly Glu Asp Trp Leu Ser Ala Lys Glu
545                 550

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Lambda
        (B) STRAIN: PaPa
        (C) INDIVIDUAL ISOLATE: Synthetic 8757

(vii) IMMEDIATE SOURCE:
        (A) LIBRARY: Primer
        (B) CLONE: MBL (viii) POSITION IN GENOME:
        (B) MAP POSITION: 27914

(xi) SEQUENCE DESCRIPTION: SEQ ID NO:7:

GCTTATCTGC TTCTCATAGA GTCTTGC                     27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Lambda
        (B) STRAIN: PaPa
        (C) INDIVIDUAL ISOLATE: Synthetic 8835

(vii) IMMEDIATE SOURCE:
        (A) LIBRARY: primer
        (B) CLONE: MBR (viii) POSITION IN GENOME:
        (B) MAP POSITION: 34570

(xi) SEQUENCE DESCRIPTION: SEQ ID NO:8:

ATAACGATCA TATACATGGT TCTCTCC                     27

(2) INFORMATION FOR SEQ ID NO:9:

(i) SEQUENCE CHARACTERISTICS:

( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Lambda
( B ) STRAIN: PaPa
( C ) INDIVIDUAL ISOLATE: Synthetic 11870

( v i i ) IMMEDIATE SOURCE:
( A ) LIBRARY: Primer
( B ) CLONE: MBL-1.7

( v i i i ) POSITION IN GENOME:
( B ) MAP POSITION: 26185

( x i ) SEQUENCE DESCRIPTION: SEQ ID NO:9:

TTTTGCTGGG TCAGGTTGTT CTTTAGG    27

( 2 ) INFORMATION FOR SEQ ID NO:10:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( v ) FRAGMENT TYPE: C-terminal ( v i ) ORIGINAL SOURCE:
( A ) ORGANISM: Eschericia coli
( B ) STRAIN: K12
( C ) INDIVIDUAL ISOLATE: Primer ( v i i ) IMMEDIATE SOURCE:
( A ) LIBRARY: Synthetic
( B ) CLONE: MSA19

( v i i i ) POSITION IN GENOME:
( B ) MAP POSITION: lacZ ( x i ) SEQUENCE DESCRIPTION: SEQ ID NO:10:

GGAAGCTTAT TTTTGACACC AGACCAAC    28

( 2 ) INFORMATION FOR SEQ ID NO:11:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:11:

GTGATGGATC CTTCAGCTTC CCGAGTTCAG CAGGCGG    37

( 2 ) INFORMATION FOR SEQ ID NO:12:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:12:

GTGCTCGAGC GAAGCTTCCC TATAGCTTTG CGAAGAG    37

( 2 ) INFORMATION FOR SEQ ID NO:13:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GAGCCATGGC CAACCTGTGG GGGAGGCTTG AGGGGGA    37

( 2 ) INFORMATION FOR SEQ ID NO:14:

( i ) SEQUENCE CHARACTERISTICS:
    ( A ) LENGTH: 36 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:14:

AGTTTGGCAG CCTCCTCCAC GAGTTCGGCC TTCTGG    36

( 2 ) INFORMATION FOR SEQ ID NO:15:

( i ) SEQUENCE CHARACTERISTICS:
    ( A ) LENGTH: 32 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:15:

GGACTGGCTC TCCGCCAAGG AGTGATACCA CC    32

( 2 ) INFORMATION FOR SEQ ID NO:16:

( i ) SEQUENCE CHARACTERISTICS:
    ( A ) LENGTH: 36 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:16:

AGTTTGGAAG CCTCCTCCAC GAGTTCGGCC TCCTGG    36

( 2 ) INFORMATION FOR SEQ ID NO:17:

( i ) SEQUENCE CHARACTERISTICS:
    ( A ) LENGTH: 35 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:17:

GGACTGGCTC TCCGCCAAGG AGTAGGGGGG TCCTG    35